United States Patent [19]
Digenis et al.

[11] Patent Number: 5,922,319
[45] Date of Patent: Jul. 13, 1999

[54] METHODS OF TREATING EYE CONDITIONS WITH HUMAN LEUKOCYTE ELASTASE (HLE) INHIBITORY AGENTS

[75] Inventors: George A. Digenis, Lexington, Ky.; Charles Khouri, Miami, Fla.

[73] Assignee: University of Kentucky Research Foundation, Lexington, Ky.

[21] Appl. No.: 07/409,894

[22] Filed: Sep. 20, 1989

[51] Int. Cl.$^6$ .................................................. A61K 38/48
[52] U.S. Cl. ........................ 424/94.64; 514/18; 514/19; 514/912; 514/913; 514/914; 514/915; 530/300
[58] Field of Search .............................. 530/300; 514/18, 514/19, 912, 913, 914, 915; 424/DIG. 13, 94.64

[56] References Cited

U.S. PATENT DOCUMENTS

| | | | |
|---|---|---|---|
| 4,609,667 | 9/1986 | Clark ........................................ | 514/367 |
| 4,613,587 | 9/1986 | Kessler ...................................... | 514/19 |
| 4,643,991 | 2/1987 | Digenis et al. ............................ | 514/18 |
| 5,008,245 | 4/1991 | Digenis .................................... | 514/18 |

OTHER PUBLICATIONS

Krummel et al. J Pediatric Surgery vol. 23. No. 7. (1988) pp. 647–652.
Siebert et al. Plastic and Reconstructive Surgery (1990) vol. 85. No. 4. pp. 495–502.
Skuta et al. Survey of Opthalmology vol. 32 No. 3. pp. 149–170, 1987.
Schmut, et al. BIOSIS Abstract No. 86:441139 1986.
Luce, J.M. Biol. Abstracts 81(3) AB–839. Abstract No. 126950 (1985).
Chesnokova N. et al. Chem Abstracts v. 105, Abstract No. 131573y (1986).
Tuhy et al., "Inhibition of Human Leukocyte Elastase by Peptide Chloromethyl Ketones,", FEBS Letters, 50, 359–61 (1975).
Powers et al., "Specificity of Porcine Pancreatic Elastase, Human Leukocyte Elastase and Cathespin G. Inhibition with Peptide Chloromethyl Ketones," Biochem. Biophys. Acta. 485, 156–66 (1977).
Dorn et al., "Proteinase Inhibitors. 1. Inhibitors of Elastase" J.Med. Chem. 20: 1464–68 (1977).
Yoshimura et al., Specificity and Reactivity of Human Leukocyte Elastase, Porcine Pancreatic Elastase, Human Granulocyte Cathespin G, and Bovine Pancreatic Chymotrpsin with Arylsulfonyl Fluorides, J. Biol. Chem 257, 5077–84 (1982).
Zimmerman et al., "Inhibition of Elastase and Other Serine Proteases by Heterocyclic Acylating Agents", J. Biol. Chem. 255: 9848–51 (1980).
Ashe et al., "Selective Inhibition of Human Leukocyte Elastase and Bovine A–Chymotrypsin by Novel Heterocycles," J. Biol. Chem. 256: 11603–6 (1981).
Scofield et al., "p–Nitrophenyl Carbamates as Active–Site–Specific Reagents for Serine Proteases," Biochemistry, 16: 2492 (1977).
Janoff et al., "Prevention of Elastase Induced Experimental Emphysemia by Oral Administration of a Synthetic Elastase Inhibitor," Am. J. Respir. Dis., 121: 1025–3 (1980).

*Primary Examiner*—Chhaya D. Sayala
*Attorney, Agent, or Firm*—McDermott, Will & Emery

[57] ABSTRACT

A method of reducing corneal scarring or fibroblast proliferation comprises applying to an area of a subject's eye afflicted with the condition a corneal scar-fibroblast proliferation-reducing amount of a free or polymer-bound HLE inhibitory agent under conditions and for a period of time effective to attain the desired effect. A method of reducing neovascularization of corneal scar tissue comprises applying to an area of a subject's eye afflicted with the condition a neovascularization-inhibitory amount of a free or polymer-bound HLE inhibitory agent under conditions and for a period of time effective to attain the desired effect.

18 Claims, 8 Drawing Sheets

METHODS OF TREATING EYE CONDITIONS WITH HUMAN LEUKOCYTE ELASTASE (HLE) INHIBITORY AGENTS

TECHNICAL FIELD

This invention relates to methods of treating corneal scarring or fibroblast proliferation by applying to the ocular area a human leukocyte elastase (HLE) inhibitory agent in a prescribed amount.

BACKGROUND OF THE INVENTION

Proteinases from polymorphonuclear leukocytes and macrophages, especially elastases (human leukocyte elastase and cathepsin G), appear to be responsible for the chronic tissue destruction associated with inflammation, arthritis and emphysema. During infection or inflammation the normal lung is protected from proteolytic digestion by the protease inhibitor $a_1$-antitrypsin. The protective mechanism appears to be non-operative in individuals with an $a_1$-antitrypsin deficiency due to genetic or other causes. Synthetic elastase inhibitors capable of replacing $a_1$-antitrypsin therefore appear to be useful in the treatment of pulmonary emphysema and related diseases.

Several types of elastase inhibitors have been reported in the literature. These include peptide chloromethyl ketones as described in "Inhibition of Human Leukocyte Elastase by Peptide Chloromethyl Ketones", P. M. Tuhy and J. C. Powers, FEBS Letters, 50, 359–61 (1975); "Specificity of Porcine Pancreatic Elastase, Human Leukocyte Elastase and Cathepsin G. Inhibition with Peptide Chloromethyl Ketones", J. C. Powers, B. F. Gupton, A. D. Harley, N. Nishino and R. J. Whitley, Biochem. Biophys. Acta. 485, 156–66 (1977); azapeptides "Proteinase Inhibitors. 1. Inhibitors of Elastase", C. P. Dorn, M. Zimmerman, S. S. Yang, E. C. Yurewicz, B. M. Ashe, R. Frankshun and H. Jones, J. Med. Chem., 20: 1464–68 (1977); "Reaction of Serine Proteases with Aza-amino Acid and Aza-peptide Derivatives", J. C. Powers and B. F. Gupton, Meth. Enzymol., 46: 208–16 (1977); sulfonyl fluorides "Specificity and Reactivity of Human Leukocyte Elastase, Porcine Pancreatic Elastase, Human Granulocyte Cathepsin G, and Bovine Pancreatic Elastase, Human Granulocyte Cathepsin G, and Bovine Pancreatic Chymotrypsin with Arylsulfonyl Fluorides"; "Discovery of a new series of potent and specific irreversible Elastase Inhibitors", T. Yoshimura, L. N. Barker and J. C. Powers, J. Biol. Chem., 257, 5077–84 (1982-); heterocyclic acrylating agents "Inhibition of Elastase and Other Serine Proteases by Heterocyclic Acylating Agents", M. Zimmerman, H. Morman, D. Mulvey, H. Jones, R. Frankshun and B. M. Ashe, J. Biol. Chem., 255: 9848–51 (1980); "Selective Inhibition of Human Leukocyte Elastase and Bovine $a_i$-Chymotrypsin by Novel Heterocycles", B. M. Ashe, R. L. Clark, H. Jones and M. Zimmerman, J. Biol. Chem., 256: 11603–6 (1981); imidazole N-carboxamides, W. C. Groutas, R. C. Badger, T. D. Ocain, D. Felker, J. Frankson and M. Theodorakis, Biochem. Biphys. Res. Commun., 95: 1890 (1980); and p-nitrophenyl-N alkyl carbamates, "p-Nitrophenyl Carbamates as Active-Site-Specific Reagents for Serine Proteases", R. E. Scofield, R. P. Werner and F. Wold, Biochemistry, 16: 2492 (1977).

Although some peptide chloromethyl ketones have been shown to be effective in preventing elastase induced emphysema in animal models there is considerable question whether such reactive agents could be used for treating emphysema in humans. ("Prevention of Elastase Induced Experimental Emphysema by Oral Administration of a Synthetic Elastase Inhibitor," A. Janoff and R. Dearing, Am. J. Respir. Dis., 121: 1025–3 (1980)). This is not surprising since the alkylating moieties in these inhibitors might render them toxic when used on a continuous basis. To be suitable for human use, an enzyme inhibitor has to show a high degree of selectively and must have minimal toxic side effects. As a result, most drugs are molecules that reversibly bind to specific enzymes or receptor sites. Examples are the carbamate esters physostigmine and neostigmine which have been clinically used as inhibitors of acetyl choline esteraces, A. G. Gilman, L. S. Goodman and A. Gilman, "The pharmacological Basis of Therapeutics", p. 101, Mac-Millan Publishing Co. (1980).

A series of peptide elastase inhibitors were disclosed in U.S. Pat. No. 4,643,991 to Digenis et al. Another group of polymer-bound elastase inhibitors was disclosed in U.S. application Ser. No. 242,294 by Digenis et al. filed on Sep. 9, 1988, now U.S. Pat. No. 5,162,307, issued Nov. 10, 1992. Still other peptidyl carbamate inhibitors of the enzyme elastase were disclosed in U.S. application Ser. No. 07/263,385 entitled "Novel Peptidyl Carbamate Inhibitors of the Enzyme Elastase" by Digenis et al., filed on Oct. 27, 1988, now U.S. Pat. No. 5,008,245, issued Apr. 16, 1991. The latter Digenis application also provides methods of inhibiting the enzyme elastase with the peptidyl carbamate agents described therein. The contents of the Digenis et al patent and applications referenced above are incorporated herein by reference to the extent that they enable the specific HLE inhibitory agents described therein and their methods of preparation.

Various conditions of the eye are known to be associated with corneal scarring and fibroblast proliferation, amongst them ocular coagulation and burns, mechanical and chemical injury, ocular infections such as kerato-conjunctivitis, and other ocular conditions. Some of these conditions are known to arise post-operatively after surgical treatment of other ocular conditions. This undesirable tissue growth is easily neovascularized and therefore becomes permanently established and irrigated. Tissue scarring or fibroblast proliferation is a condition which is difficult to treat. Presently, it is treated by subjecting the ocular area to further surgery or by using steroids, topically or by injection. However, steroids do increase side effects such as infection, cataract and glaucoma. Other non-steroidal agents like indomethcin have very little anti-scarring effects. (Williamson J. et al., British J. of Ophthalmology 53:361 (1969); Babel, J., Histologie Der Crtisonkatarakt, p.327. Bergmann, Munich (1973)).

Even after further surgery the proliferation of fibroblastic tissue continues to occur and further scar tissue appears. Thus, in addition to surgery being an extremely invasive procedure, the results attained thereof are not entirely satisfactory.

Accordingly, there remains a need in the art for methods of reducing and/or preventing the formation of corneal scar tissue or fibroblast proliferation which are not subject to the disadvantages of methods known in the art for this purpose.

SUMMARY OF THE INVENTION

This invention relates to a method of reducing corneal scarring or fibroblast proliferation comprising applying to an area of a subject's eye afflicted with the condition a corneal scar- or fibroblast proliferation-reducing amount of a human leukocyte elastase (HLE) inhibitory agent under conditions and for a period of time effective to attain the desired effect.

Also part of this invention is a method of reducing neovascularization of corneal scar tissue comprising applying to an area of a subject's eye afflicted with the condition a neovascularization-inhibitory amount of an HLE inhibitory agent under conditions and for a period of time effective to attain the desired effect.

A more complete appreciation of the invention and many of the attendant advantages thereof will be readily perceived as the same becomes better understood by reference to the following detailed description when considered in connection with the accompanying figures.

Figure 1:
FIG. 1 is a print of a histological microscopic photograph of a corneal tissue as described in Table 2. This photograph shows a pathology section of an untreated corneal burn. Excessive inflammation and fibroblastic activity (thin arrows) can be seen. Severe neovascular formation is marked with thick short arrows (H&E Stain ×200).
Figure 2:
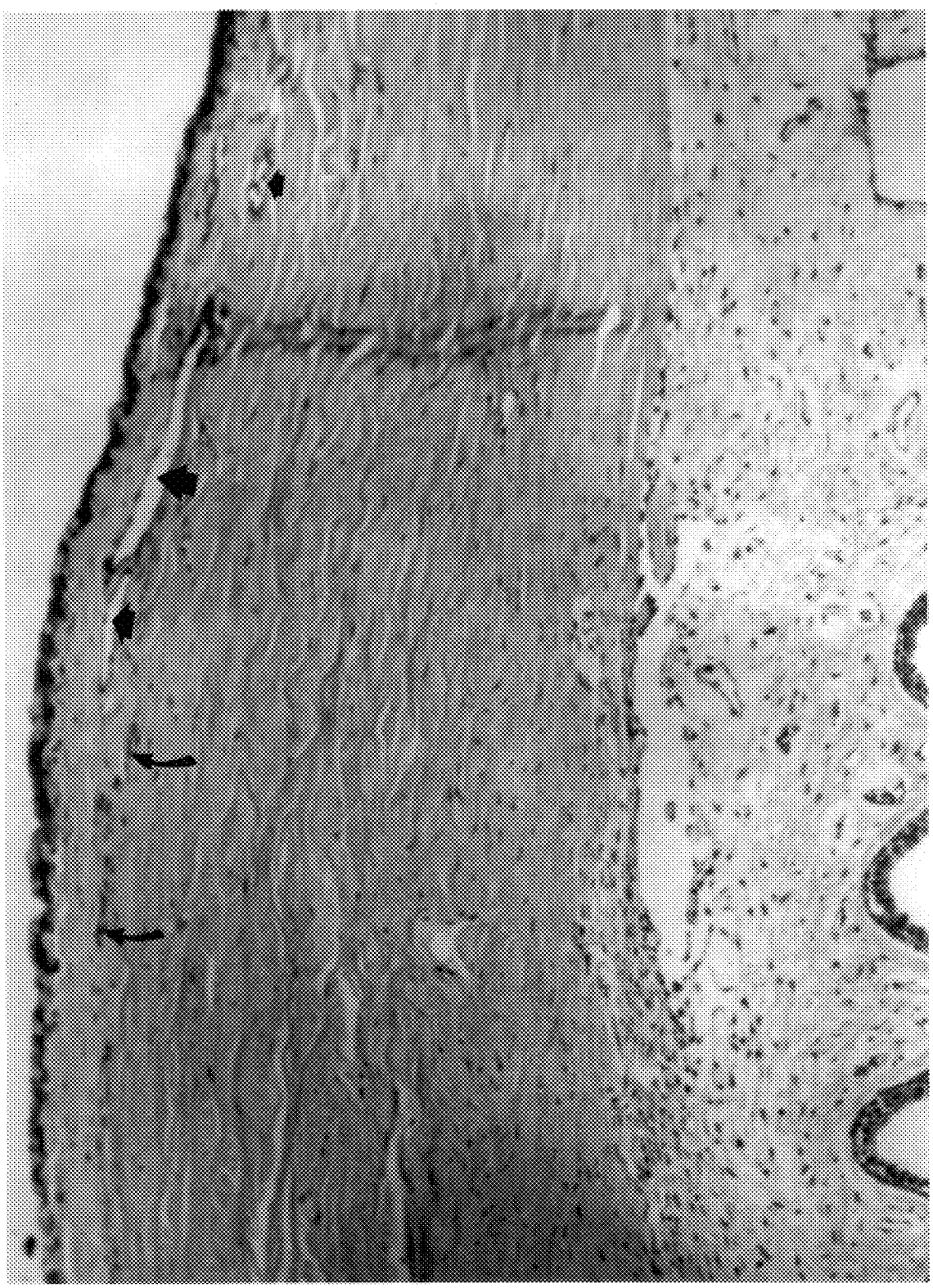
FIG. 2 is a print of a histological microscopic photograph of a corneal tissue described in Table 2. This photograph shows a pathology section of a corneal burn treated with the inhibitor of this invention. As can be seen, the degree of inflammation, scarring and neovascular formation is minimal and has been greatly reduced when compared with FIG. 1, the control eye (H&E Stain ×200).
Figure 3:
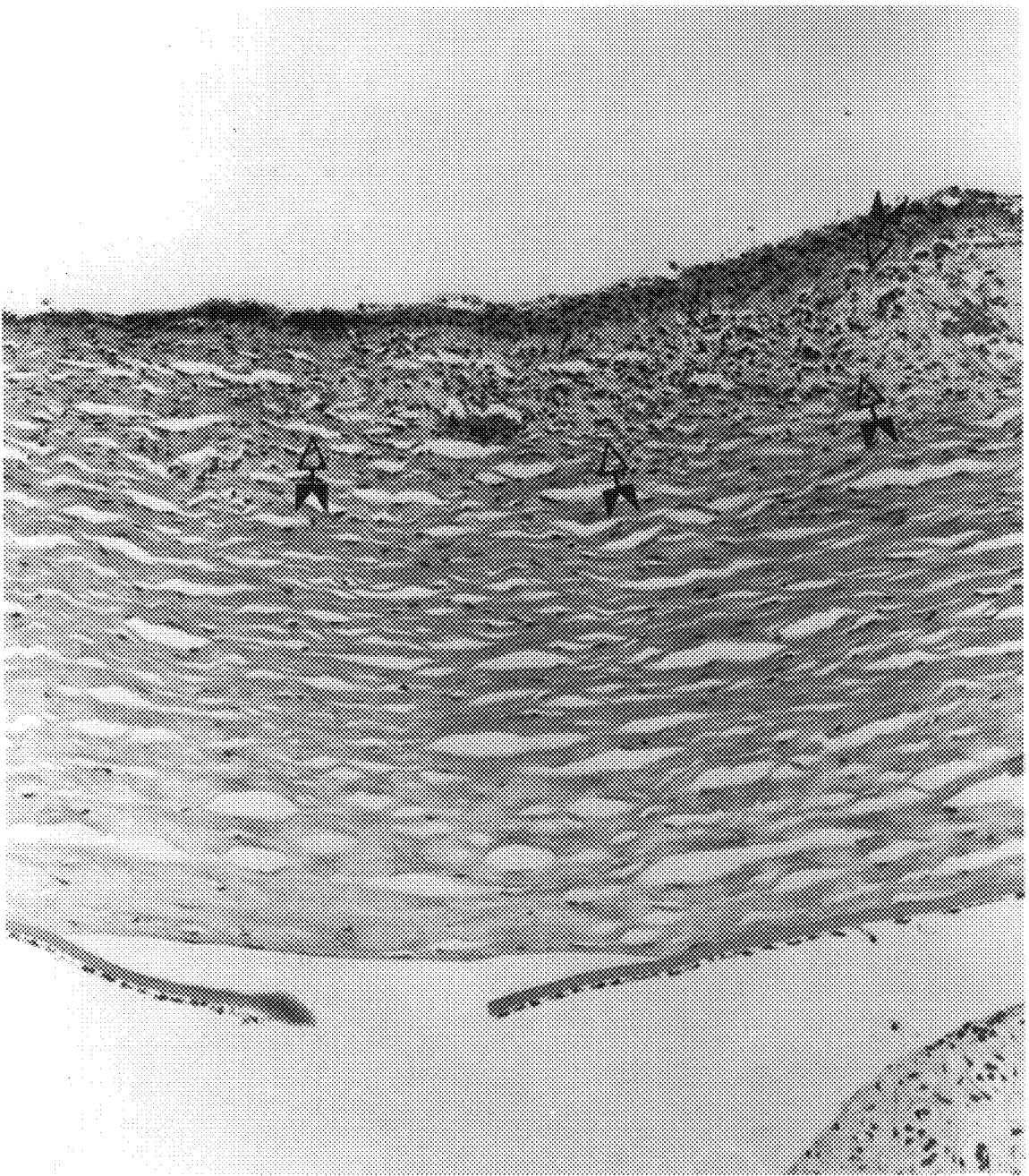
FIGS. 3, 5 and 7 are pathology sections of rabbit corneas that were thermally burned and treated for two weeks with polyvinyl alcohol. Severe inflammatory reaction is seen including formation of polymorphonuclear neutrophils, eosinophils, fibroblasts, and granulation tissue (arrows) (Hematoxylin and eosin ×100).
Figure 4:
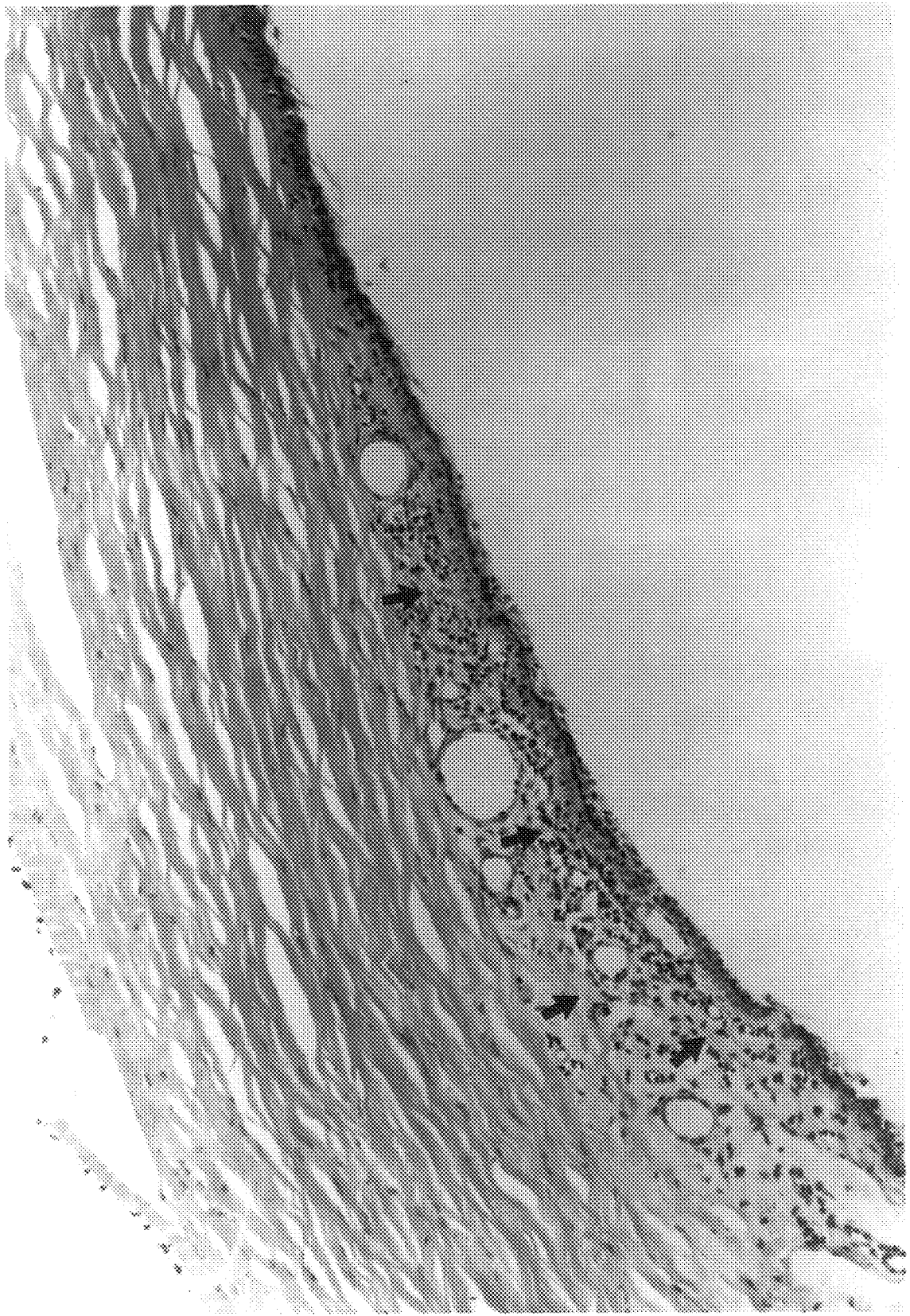
FIGS. 4, 6 and 8 show pathology sections of rabbit corneas that were thermally burned and treated with the inhibitor of this invention for two weeks. As can be seen, the inflammatory reaction is much reduced in comparison to the control eyes (untreated) shown in FIGS. 3, 5 and 7. Inflammation, scarring and neovascularization are much reduced when compared with the control eyes (Hematoxylin and eosin ×100).
Figure 5:
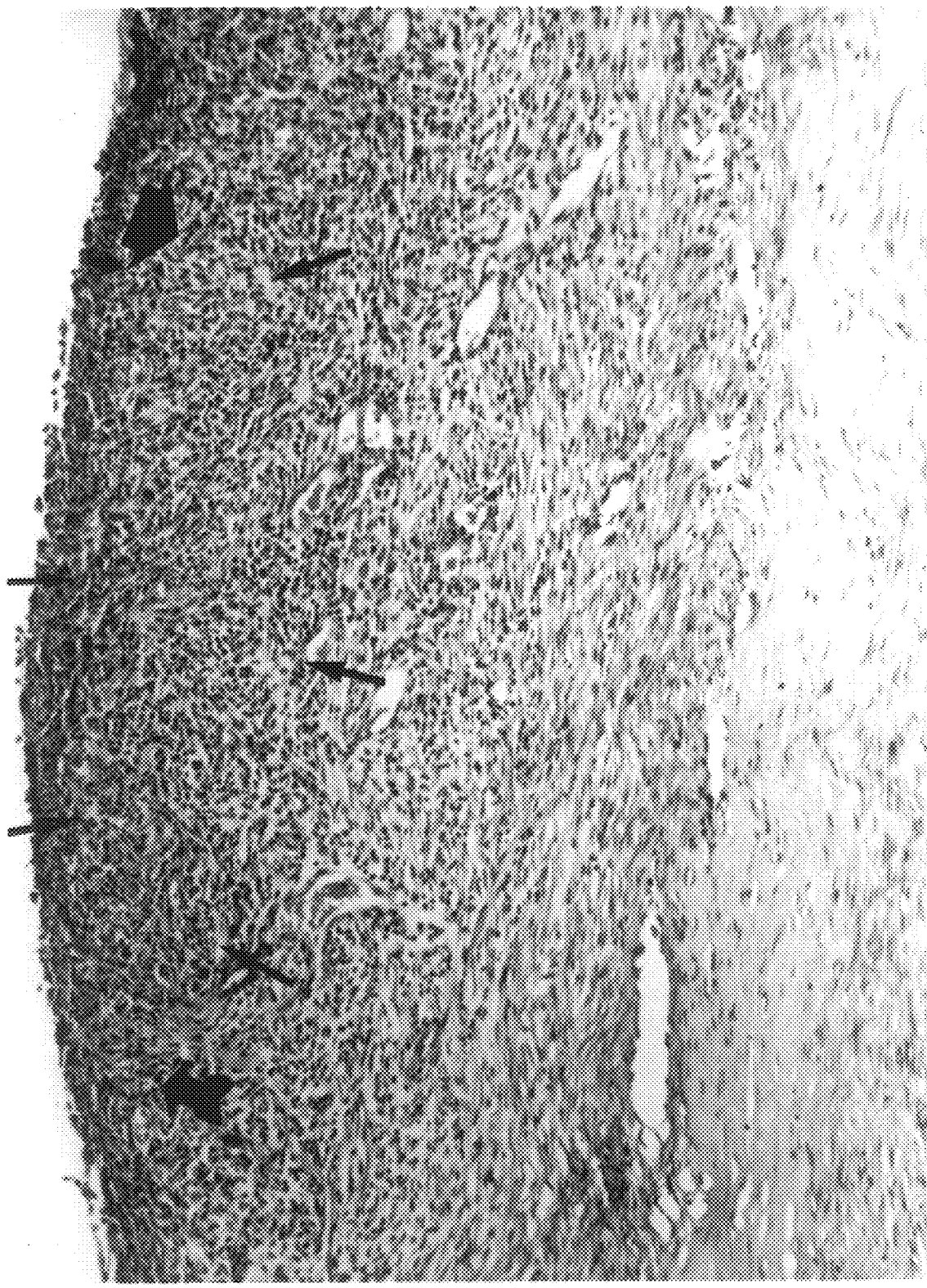
Figure 6:
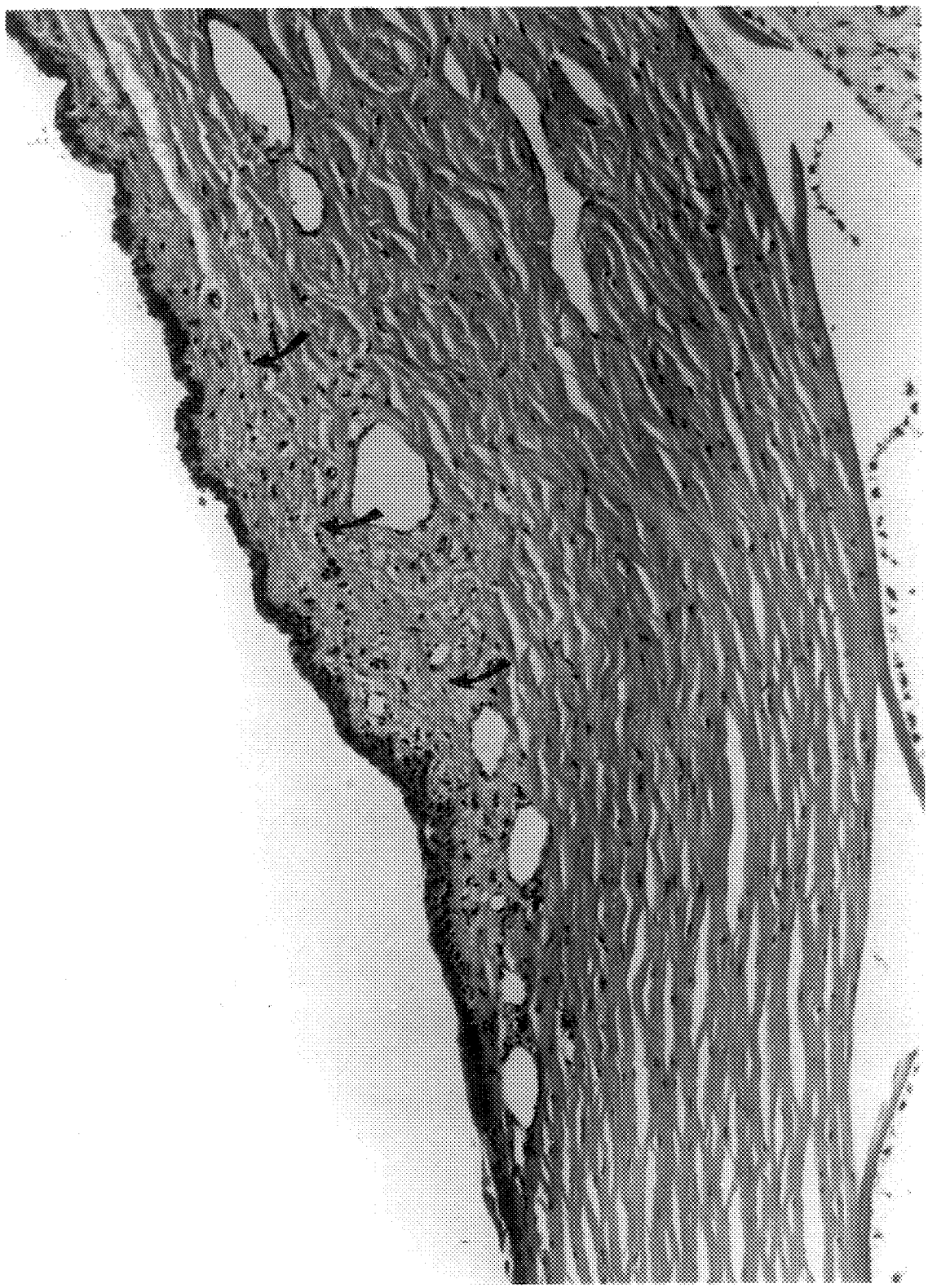
Figure 7:
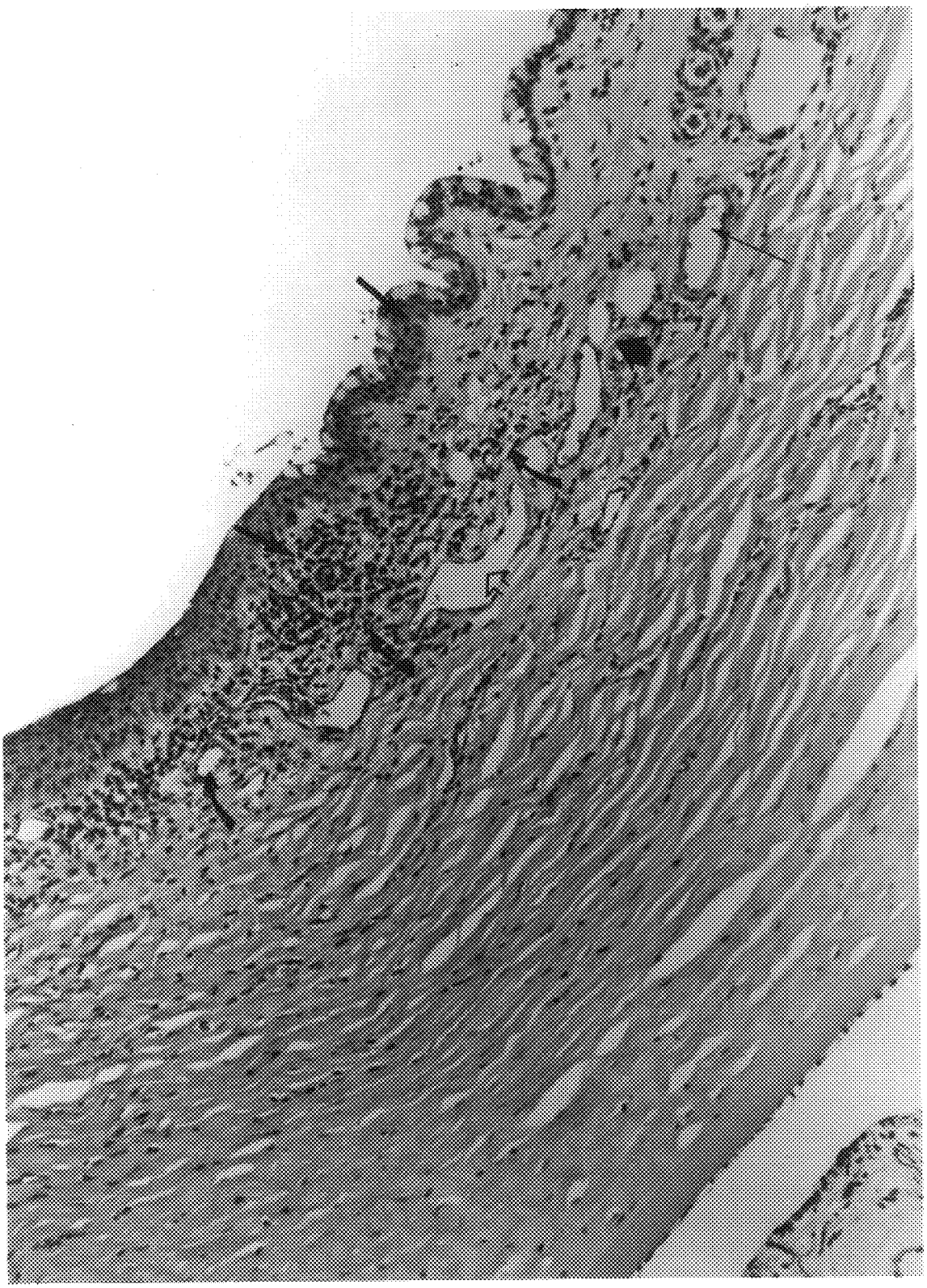
Figure 8:
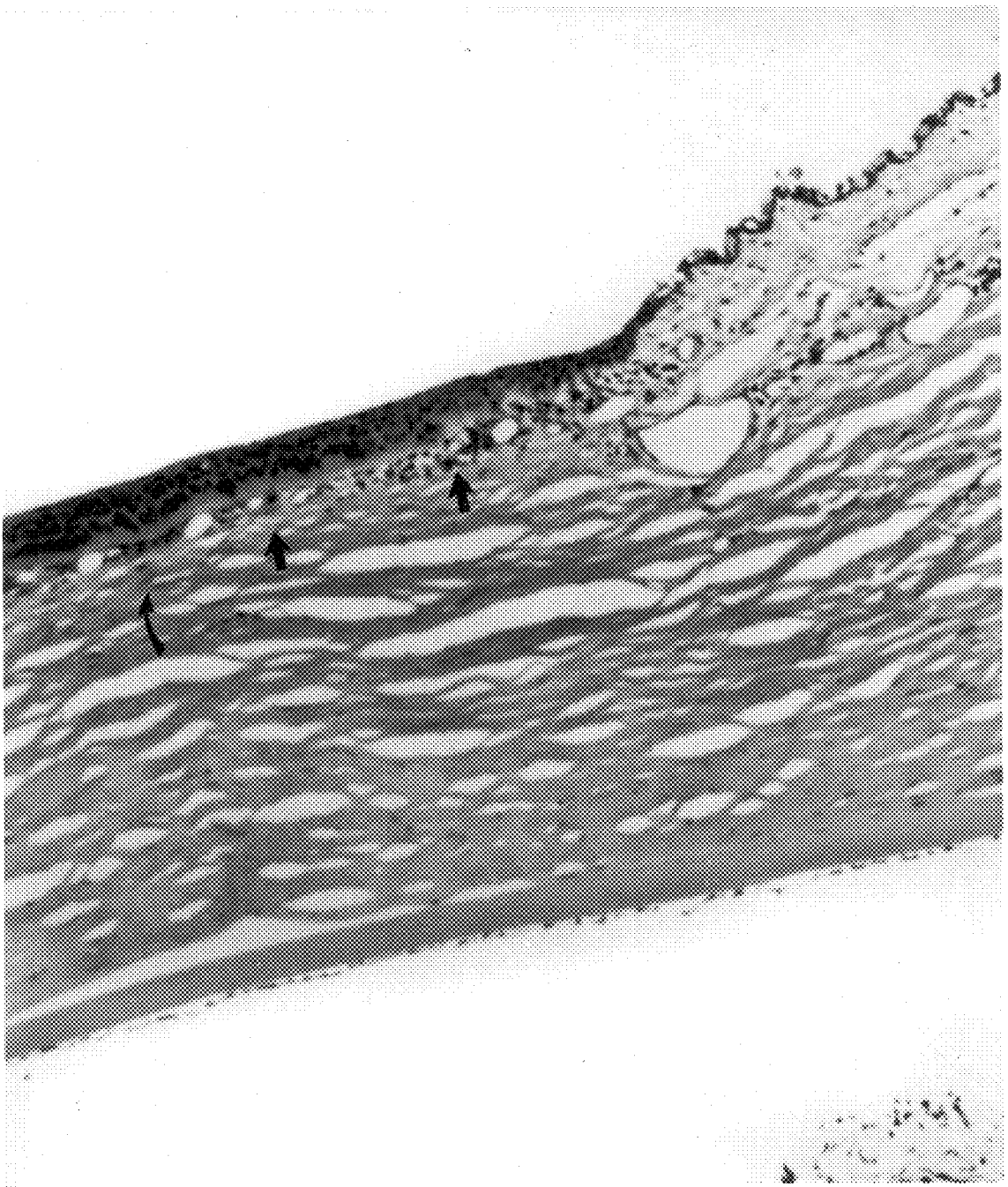

Other objects, advantages and features of the present invention will become apparent to those skilled in the art from the following discussion.

BEST MODE FOR CARRYING OUT THE INVENTION

This invention arose from a desire to improve over prior art methods for treating ocular scarring or fibroblast proliferation, particularly when it occurs in the cornea of the eye.

The inventors have found for the first time that if an HLE inhibitory agent is applied to a subject's eye it has an inhibitory effect on the proliferation and growth of fibroblasts or scar tissue. For the first time the inventors have shown that HLE inhibitors have an ophthomological application.

Thus, the present invention relies on the therapeutic application of HLE inhibitory agents to the corneal area of the eye to prevent and/or reduce corneal scarring or fibroblast proliferation as well as new vascularization. These conditions have been found to be associated with a variety of pathological states of the eye such as infections, burns and mechanical and chemical injury, among others.

The inhibitory agents utilized in the present methods may be applied to the eye topically, intraocularly, by injection or through a contact lens. Preferred is topical. By means of example the agents may be applied as a solution in a solvent which is not detrimental to the functions of the eye. Typically, an aqueous solution of the HLE inhibitory agent may be utilized. However, given that some HLE inhibitory agents are cleared very limpidly from the eye, they may also be bound to a water soluble or hydrophilic polymer to ensure a more prolonged residence in the desired area. The aqueous solution may also contain other ingredients as is known in the art.

This invention thus provides a method of reducing corneal scarring or fibroblast proliferation which comprises applying to an area of a subject's eye afflicted with the condition a corneal scar- or fibroblast proliferation-reducing amount of an HLE inhibitory agent under conditions and for a period of time effective to attain the desired effect.

Any HLE inhibitory agent may be utilized when practicing the method of the invention. Typically, many HLE inhibitory agents are known in the art as discussed above and need not be further described herein. By means of example, inhibitory agents which are suitable for use with this invention are those described in U.S. Pat. No. 4,643,991 and U.S. Pat. No. 5,008,245 both to Digenis et al. A series of peptide elastase inhibitors were disclosed in U.S. Pat. No. 4,643,991 to Digenis et al. These peptide elastase inhibitors are carbamates substituted by oligopeptides and may generally be described by the following general formula (I):

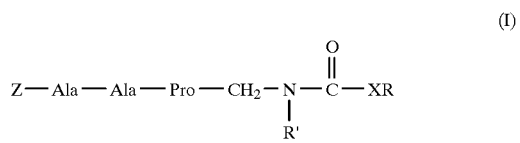

(I)

wherein Z is selected from the group consisting of R"O-Suc- where R" is lower alkyl of 1 to 3 carbon atoms and $CF_3CO$—; X is oxygen or sulfur, R' is selected from the group consisting of straight or secondary branched-chain alkyl of 1 to 4 carbon atoms, alkenyl of 1 to 4 carbon atoms, alkynyl of 2 to 4 carbon atoms, cycloalkyl of 3 to 6 carbon atoms, preferably cyclopropyl or cyclohexyl, and benzyl, and R is selected from the group consisting of substituted or unsubstituted phenyl wherein the substituents are selected from the group consisting of nitro, preferably p-nitro, and fluoro, preferably pentafluoro, benzyl, $CH_2CF_2CF_2CF_3$, 1-lower alkyl tetrazolyl-, 1-phenyltetrazolyl-, 2-thioxo-3-thiazolindyl, pyridyl, and benzothiazolyl, provided that when R is paranitrophenyl, R' is other than tertiary-butyl, benzyl or cyclohexyl, and when X is sulfur, R is other than benzyl.

In more preferred embodiments, the inhibitory peptides may be described by the following general formulae Ia or Ib:

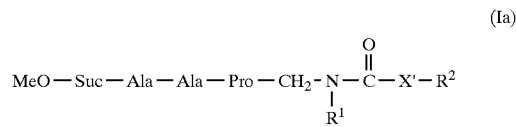

(Ia)

wherein X' is oxygen or sulfur and $R^2$ is selected from the group consisting of phenyl, fluorophenyl, nitrophenyl, 1-phenyltetrazolyl, 1-lower alkyl tetrazolyl, benzyl, 3-thiazolidinyl, pyridyl, and benzothiazolyl, and $R^1$ is straight or secondary branch chained alkyl of 2 to 4 carbons, alkenyl of 2 to 4 carbons, and alkynyl of 2 to 4 carbons, provided that when $R^2$ is p-nitrophenyl, $R^1$ is other than tertiary-butyl, and when X' is sulfur, $R^2$ is other than benzyl; and

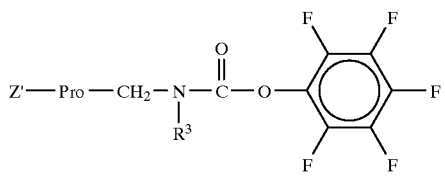

(Ib)

wherein Z' is selected from the group consisting of MeO-Suc-Ala-Ala and $CF_3CO$-Ala-Ala, wherein $R^3$ is as defined for $R^1$ above, but is preferably isopropyl.

However, other HLE inhibitory agents may also be utilized for practicing the present method.

As already indicated above, the HLE inhibitory agents may be bound to a hydrophilic or water-soluble polymer in order to extend their residence in the area to which they are applied. The HLE inhibitory agents may be covalently bound to any hydrophilic and/or water-soluble polymer which does not detrimentally affect the function of the eye. Many such polymers are known in the art and discussed in U.S. Pat. No. 5,162,307 to Digenis et al. The polymer-bound HLE inhibitory agent described in the referenced application are suitable for practicing this invention. An example of the group of polymer-bound elastase inhibitors useful in the present invention, as disclosed in U.S. Pat. No. 5,162,307 to Digenis et al., have the following structures:

A Polymer of the formula

(II)

wherein P is a polymer comprising at least one unit of the formula $(A_mB_n)$ wherein $(A_mB_n)$ is substantially nonbiodegradable and has an average molecular weight of about 1,000 to 500,000 daltons, m and n may be the same or different and are about 5 to 3,000, and A and B may be the same or different and at least one of A and B is capable of covalently binding to one of L and $R^4$;

wherein $R^4$ is a compound selected from the group consisting of (i) a compound C of the formula

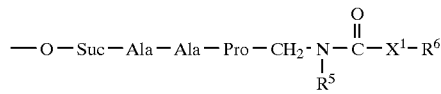

(C)

wherein
$X^1$ is oxygen or sulfur;
$R^5$ is selected from the group consisting of straight and secondary branch-chained $(C_1-C_4)$ alkyl, $(C_2-C_3)$ alkenyl, $(C_2-C_4)$ alkynyl, $(C_3-C_6)$ cycloalkyl, and benzyl; and
$R^6$ is selected from the group consisting of substituted and unsubstituted phenyl, wherein the substituents are selected from the group consisting of nitro, and pentafluoro, benzyl, $CH_2CF_2CF_2CF_3$, 1-lower alkyl tetrazolyl, 1-phenyltetrazolyl, 2-thioxo-3-thiazolidinyl, pyridyl and benzothiazolyl, provided that when $R^6$ is p-nitrophenyl $R^5$ is other than tert-butyl, benzyl or cyclohexyl, and when $X^1$ is sulfur $R^6$ is other than benzyl:

(ii) a compound D of the formula:

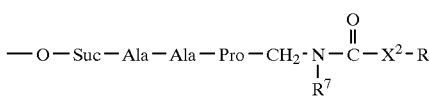

(D)

wherein
$X^2$ is O or S.
$R^8$ is selected from the group consisting of phenyl, nitrophenyl, fluorophenyl, $CH_2CF_2CF_2CF_3$, 1-lower alkyltetrazolyl, 1-phenyltetrazolyl, benzyl, 2-thioxo-3-thiaxo-3-thiazolidinyl, pyridyl and benzothiazolyl, and
$R^7$ is selected from the group consisting of straight or secondary branch chained $(C_1-C_4)$ alkyl, $(C_2-C_3)$ alkenyl, $(C_2-C_4)$ alkynyl, $(C_3-C_6)$ cycloalkyl, and benzyl, provided that when $R^8$ is p-nitrophenyl $R^7$ is other than tertiary-butyl, benzyl or cyclohexyl, and when $X^2$ is sulfur $R^8$ is other than benzyl; and (iii) a compound E of the formula

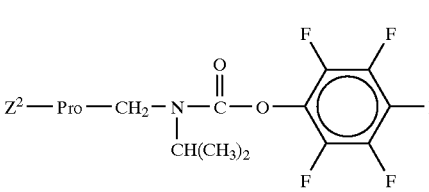

(E)

wherein
$Z^2$ is —O—Suc-Ala-Ala:
each said $R^4$ being covalently bound to L or to one of A and B,
L is selected from the group consisting of a covalent bond and a linker group which is covalently bound to $R^4$ and one of A and B; and
q is about 1 to m+n.

More preferred compounds according to the U.S. Pat. No. 5,162,307 are compounds wherein
A is a compound of the formula

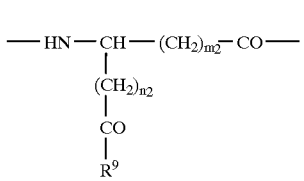

(IIa)

wherein $m_2=0$ or 1 and $n_2=1$ or 0 respectively and $R^9$ is selected from the group consisting of OH, 2-hydroxyethyl amine, 2-hdroxypropylamine, 3-hydroxypropyl amine, 2,3-dihydroxypropyl amine, 2-hydroxybutylamine and 4-hydroxybutylamine; and B is a compound of the formula (IIa) above, wherein $R^9$ is selected from the group consisting of $NH_2$, $NH—NH_2$, $NH—NH_2$, $—NH—R^{10}—NH_2$ wherein $R^{10}$ is $(C_2-C_{10})$ alkyl or $(C_6-C_8)$ aryl, and $NH—R^{11}—OH$ wherein $R^{11}$ is $(C_2-C_8)$ alkyl or $(C_6-C_8)$ aryl.

Particularly preferred are compounds wherein the polymer P is poly-$\alpha_1\beta$-(N(2-hydroxyethyl)-D,L-asparagine), a copolymer derived from poly(N-2-vinylpyrrolidone) or a polysaccharide selected from the group consisting of dextran, carboxymethyl cellulose, alginic acid and hyduronic acid.

Also preferred in U.S. Pat. No. 5,162,307 are compounds wherein

A is selected from the group consisting of N-2-vinylpyrrolidone, N-hydroxypropylmethacrylamide, 2-hydroxyethyl methacrylate and acrylamide, B is selected from the group consisting of amino ($C_2$–$C_6$) alkylmethacrylamide, amino ($C_2$–$C_6$) alkylacrylamide, amino ($C_2$–$C_6$) alkyl maleic acid monoamide, O-alkyl acrylate and methacrylate where alkyl is of the general formula $CH_2$—$CH(OH)$—$CH_2$—$NH$—$R^{12}$—$NH_2$ where $R^{12}$ is $C_2$–$C_6$ hydrocarbon.

Even more preferred in the U.S. Pat. No. 5,162,307 are compounds wherein

A and B are one and the same.

The most preferred and particular species of compounds as stated in the U.S. Pat. No. 5,162,307 are incorporated herein by reference thereto.

Still other peptide or peptidyl carbamate inhibitors of the enzyme elastase were disclosed in U.S. Pat. No. 5,008,245 to Digenis et al., which are useful in the present invention and have the following structures:

$X^3R^{15}$ is

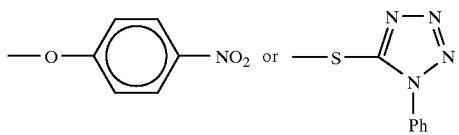

A compound selected from the group consisting of a compound of the formula

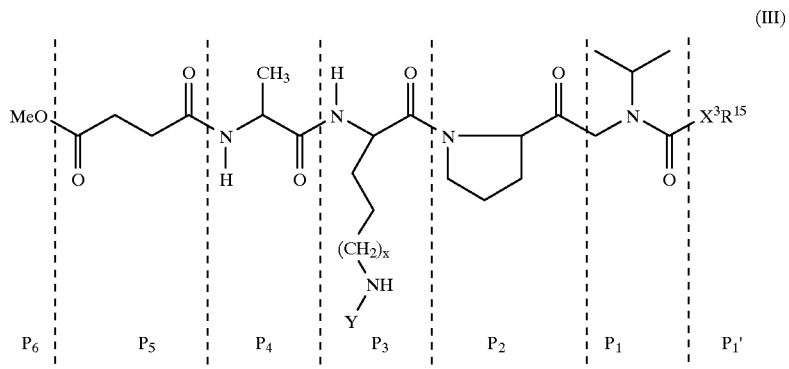

(III)

wherein x is 1 or 2;

Y is carbobenzoxy or benzoyl; and

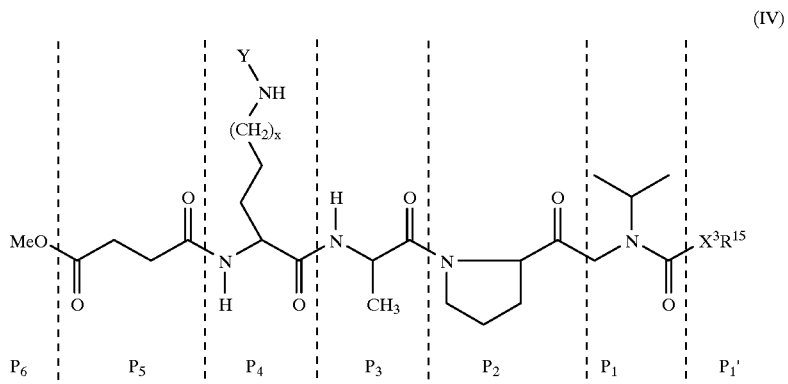

(IV)

wherein
x is 1 or 2;
Y is carbobenzoxy or benzoyl; and
$X^3R^{15}$ is

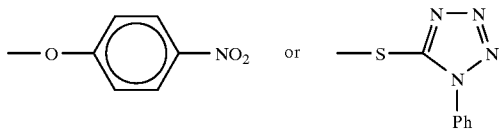

More preferred are compounds having the following structure

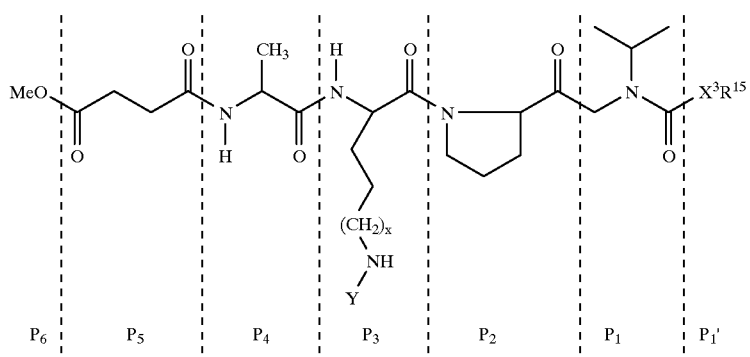

wherein x is 1 or 2; Y is carboxybenzoxy or benzoyl; and $X^3R^{15}$ is

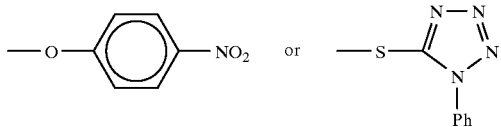

Even more preferred are:
(1) p-Nitrophenyl N-[(Methoxysuccinyl)-L-alanyl-L-alanyl-L-prolylmethyl]-N-isopropylcarbamate,
(2) Methyl succinimide succinate,
(3) t-Butyl Methoxysuccinyl-L-alanine ester,
(4) Methoxysuccinyl-L-alanine,
(5) $N_\alpha$-Methyoxysuccinyl-L-alanyl-$N_\epsilon$-benzoyl-L-lysine,
(6) $N_\alpha$-Methoxysuccinyl-L-alanyl-$N_\epsilon$-carbobenzoxy-L-lysine, phenacyl ester,
(7) $N_\alpha$-Methoxysuccinyl-L-alanyl-$N_\epsilon$-carbobenzoxy-L-lysine,
(8) $N_\alpha$-Methoxysuccinyl-L-alanyl-$N_\delta$-carbobenzoxy-L-ornithine phenacyl ester,
(9) $N_\alpha$-Methoxysuccinyl-L-alanyl-$N_\delta$carbobenzoxy-L-ornithine,
(10) $N_\alpha$-Methoxysuccinyl-$N_\delta$-carbobenzoxy-L-ornithine,
(11) $N_\alpha$-Methoxysuccinyl-$N_\delta$-carbobenzoxy-L-ornithyl-L-alanine t-butyl ester,
(12) $N_\alpha$-Methoxysuccinyl-$N_\delta$-carbobenzoyl-L-ornithyl-L-alanine,
(13) $N_\alpha$-methoxysuccinyl-$N_\epsilon$-carbobenzoxy-L-lysine,
(14) $N_\alpha$-Methoxysuccinyl-$N_\epsilon$-carbobenzoxy-L-lysyl-L-alanine t-butyl ester,
(15) $N_\alpha$-Methoxysuccinyl-$N_\epsilon$ carbobenzoxy-L-lysyl-L-alanine,
(16) $N_\alpha$-Methoxysuccinyl-$N_\epsilon$-benzoyl-L-lysine,
(17) $N_\alpha$-methoxysuccinyl-$N_\epsilon$-benzoyl-L-lysyl-L-alanine t-butyl ester,
(18) $N_\alpha$-Methoxysuccinyl-$N_\epsilon$-benzoyl-L-lysyl-L-alanine,
(19) N-Boc-L-prolyl chloromethyl ketone,
(20) N-[(N-Boc-L-prolyl)methyl]isopropylamine,
(21) N-[(N-Boc-L-prolyl)methyl]-N-isopropylcarbamate,
(22) p-Nitrophenyl N-(L-prolylmethyl)-N-isopropylcarbamate hydrochloride,
(23) $N_\alpha$-Methoxysuccinyl-L-alanyl-$N_\epsilon$-carbobenzoxy-L-lysyl-D-proline phenacyl ester,
(24) $N_\alpha$-Methoxysuccinyl-L-alanyl-$N_\epsilon$-carbobenzoxy-L-lysyl-L-proline phenacyl ester,
(25) $N_\alpha$-Methoxysuccinyl-L-alanyl-$N_\epsilon$-carbobenzoxy-L-lysyl-D-proline,
(26) $N_\alpha$-Methoxysuccinyl-L-alanyl-$N_\epsilon$ carbobenzoxy-L-lysyl-L-proline,
(27) $N_\alpha$-Methoxysuccinyl-L-alanyl-$N_\epsilon$-carbobenzoxy-L-lysyl-D-prolyl chloromethyl ketone,
(28) $N_\alpha$-Methoxysuccinyl-L-alanyl-$N_\epsilon$-carbobenzoxy-L-lysyl-L-prolyl chloromethyl ketone,
(29) N-[Methoxysuccinyl-L-alanyl-($N_\epsilon$-carbobenzoxy)-L-lysyl-D prolylmethyl]-N-isopropylamine,
(30) N-[Methoxysuccinyl-L-alanyl-($N_\epsilon$-carbobenzoxy)-L-lysyl-L-prolylmethyl]-N-isopropylamine,
(31) $N_\alpha$-t-Boc-$N_\epsilon$-carbobenzoxy-L-lysine,
(32) $N_\alpha$-t-Boc-$N_\epsilon$-carbobenzoxy-L-lysine phenacyl ester,
(33) $N_\epsilon$-Carbobenzoxy-L-lysine phenacyl ester hydrochloride,
(34) $N_\alpha$-t-Boc-$N_\delta$-carbobenzoyl-L-ornithine,
(35) $N_\alpha$-t-Boc-$N_\delta$-carbobenzoyl-L-ornithine phenacyl ester,
(36) $N_\delta$-carbobenzoxy-L-ornithine phenacyl ester hydrochloride,
(37) N-t-Boc-D-proline,
(38) N-t-Boc-L-proline,
(39) N-t-Boc-D-proline phenacyl ester,
(40) N-t-Boc-L-proline phenacyl ester,
(41) D-Proline phenacyl ester hydrochloride,
(42) L-Proline phenacyl ester hydrochloride,
(43) $N_\epsilon$-Benzoyl-L-lysine,
(44a) p-Nitrophenyl N-[Methoxysuccinyl-($N_\epsilon$-carbobenzoxy)-L-lysyl-L-alanyl-L-prolylmethyl]-N-isopropylcarbamate,
(44b) p-Nitrophenyl N-[Methoxysuccinyl-($N_\epsilon$-carbobenzoxy)-L-lysyl-L-alanyl-D-prolylmethyl]-N-isopropylcarbamate,
(45a) p-Nitrophenyl N-[Methoxysuccinyl-($N_\epsilon$-benzoyl)-L-lysyl-L-alanyl-L-prolylmethyl]-N-isopropylcarbamate,
(45b) p-Nitrophenyl N-[Methoxysuccinyl-$N_\epsilon$-benzoyl)-L-lysyl-L-alanyl-D-prolylmethyl]-N-isopropylcarbamate, (46a) p-Nitrophenyl N-[Methoxysuccinyl-($N_\delta$-carbobenzoxy)-L-ornithyl-L-alanyl-L-prolylmethyl]-N-isopropylcarbamate (46b) p-Nitrophenyl-($N_\delta$-carbobenzoxy)-L-ornithyl-L-alanyl-D-prolylmethyl]-N-isopropylcarbamate, (47a) p-Nitrophenyl N-[Methoxysuccinyl-($N_\delta$-benzoyl)-L-ornithyl-L-alanyl-L-prolylmethyl]-N-isopropylcarbamate, (47b) p-Nitrophenyl N-[Methoxysuccinyl-($N_\delta$-benzoyl)-L-ornithyl-L-alanyl-D-prolylmethyl]-N isopropylcarbamate, (48a) p-Nitrophenyl N-[Methoxysuccinyl-L-alanyl-($N_\epsilon$-carbobenzoxy)-L-prolylmethyl]-N-isopropylcarbamate, (48b) p-Nitrophenyl N-[Methoxysuccinyl-L-alanyl-($N_\epsilon$-carbobenzoxy)-L-lysyl-D-prolylmethyl]-N-isopropylcarbamate, (49a) p-Nitrophenyl N-[Methoxysuccinyl-L-alanyl-($N_\epsilon$-benzoyl)-L-lysyl-L-prolylmethyl]-N-isopropylcarbamate, (49b) p-Nitrophenyl N-[Methoxysuccinyl-L-alanyl-($N_\epsilon$-benzoyl)-L-lysyl-D-prolylmethyl]-N-isopropylcarbamate, (50a) p-Nitrophenyl N-[Methoxysuccinyl-L-alanyl-($N_\delta$-carbobenzoxy)-L-ornithyl-L-prolylmethyl]-N-isopropylcarbamate, (50b) p-Nitrophenyl N-[Methoxysuccinyl-L-alanyl-($N_\delta$-carbobenzoxy)-L-ornithyl-D-prolylmethyl]-N-isopropylcarbamate, (51a) p-Nitrophenyl N-[Methoxysuccinyl-L-alanyl-($N_\delta$-benzoyl)-L-ornithyl-L-prolylmethyl]-N-isopropylcarbamate, (51b) p-Nitrophenyl N-[Methoxysuccinyl-L-alanyl-($N_\delta$-benzoyl)-L-ornithyl-D-prolylmethyl]-N-isopropylcarbamate,

(52) S-(1-phenyl-5-tetrazol) chloroformate,

(53) S-(1-phenyl-5-tetrazoyl)-N-[(N-Boc-L-prolyl)methyl]-N-isopropylthiocarbamate,

(54) S-(1-phenyl-5-tetrazoyl-N-prolymethyl)-N-isopropylthiocarbamate hydrochloride, (PC5) S-(1-phenyl-5-tetrazoyl)-N-[methoxysuccinyl-alanyl-($N_\epsilon$-Carbobenzoxy) lysyl prolyl methyl]-N-isopropyl-thiocarbamate, or (PC6) S-(1-phenyl-5-tetrazoyl)-N-[methoxysuccinyl-(N-carbobenzoyl)ornithylalanyl (prolylmethyl)-N-isopropylthio carbamate.

Also suitable, however, are other polymer-bound HLE inhibitory agents which can be prepared by chemically binding known HLE inhibitory agents to somewhat hydrophilic and/or water-soluble polymers as an artisan would know, and is for example described in U.S. Pat. No. 5,162,307 to Digenis et al, described supra.

In general, the polymers suitable for use in this invention are water soluble polymers, and preferably, polymers having a flexible backbone structure which are not easily biodegradable and which consequently have a prolonged biological half life. Even more preferred are polymers which are water soluble and substantially non-biodegradable but which also have a flexible polymer backbone. A high flexibility exhibited by the polymer is helpful in increasing the accessibility of the polymer bound inhibitory molecule to the enzyme.

Suitable polymers for use in this invention are polymers containing amide bonds in the main chain. Particularly useful are derivatives of synthetic polyaminoacids, examples of which include random copolymers of α, β hydroxy alkyl-D,L-aspartamide, e.g., poly α, β-(N-(2-hydroxyethyl)-D,L-aspartamide) in which a fraction of 2-hydroxyethyl side-chains is replaced by appended reactive moieties having HLE inhibitory activity.

Other examples of suitable polymers include polysaccharide derivatives, especially derivatives of dextran, cellulose, carboxymethyl cellulose, alginic acid and hyaluronic acid, combinations thereof or combinations with other polymers. Yet another example of suitable polymers with oxygen atoms in the main polymer chain are polyether polymers, examples of which include polyethyleneglycol (polyoxirane), divinylethermaleic acid copolymer (pyran copolymer, DIVEMA), and the like. Examples of polymers with a-CC-backbone suitable for use in this invention are copolymers prepared from mixtures of different types of monomers. One such group is a polymer formed by mixing one type of monomer which has active appended moieties and another type of monomer lacking such moieties. Particularly suitable are copolymers derived from hydrophilic vinylic and/or acrylic type monomers. Examples include N-2-vinylpyrrolidone, 2hydroxzypropylmethacrylamide, 2hydroxyethylmethacrylate and other hydrophilic esters and amides of acrylic and methacrylic acid which are well known in the art. Suitable monomers containing appended reactive moieties for preparation of copolymers for use in this invention include, e.g., maleic acid anhydride and reactive esters of acrylic and methacrylic acid. Particularly suitable are, e.g., glycidyl acrylate, glycidyl methacrylate, p-nitrophenyl, N-hydroxysuccinimide, pentachlorophenyl or/and pentafluorophenyl esters of methacrylic and acrylic acids, wherein the alkoxy moiety of the reactive ester can be either bound directly to the carbonyl of methacrylic or acrylic acid or it can be bound via a spacer or linker.

Suitable spacers or linkers for use in these types of polymers are generally known in the art. Examples of particularly suitable polymers include poly(N-vinylpyrrolidone), co-poly-(N-vinylpyrrolidone-co-maleic acid anhydride), co-poly- (N-vinylpyrrolidone-co-methacryloyl-N-hydroxysuccinimide, co-poly(N-(2-hydroxypropyl)methacrylamide-co-methacryloyl p-nitrophenyl ester) and other copolymers formed by the monomers indicated above.

The polymers utilized for practicing the present invention must be pharmaceutically-acceptable polymers. These are known in the art as such.

Where the HLE inhibitory agents are attached to the polymer by means of a linker or spacer the linkers or spacers must contain at least two reactive groups. One of the reactive groups must be capable of covalently bonding to the appended moiety present in at least some of the monomer units contained in the polymer. The other reactive group must be capable of covalently bonding to a reactive group present in the free HLE inhibitory agent molecule which is not involved in the binding to the active site of the enzyme. Suitable linkers are known in the art and need not be specifically described herein. One group of linkers which has been found suitable for use with this invention is that encompassing flexible backbone hydrocarbons containing at least two reactive groups. Suitable are reactive groups such as hydroxyl, sulfhydryl, amino, carboxyl, hydrazino and hydrozido, among others. However, other groups may also be utilized. The length of the linker or spacer may vary as desired for particular applications. Typically, ($C_2$–$C_{20}$) hydrocarbon linkers are utilized, preferably linear hydrocarbons. However, other types of molecules may also be incorporated herein.

Particularly suitable types of linker or spacer has been found to be those comprising ($C_2$–$C_{20}$) hydrocarbons having covalently bonded substituents to the first and last carbon atoms such as hydroxylamines. Other examples suitable for use in this invention are α, -diamines, α, -diamino alcohols and α, -diamino acids. By means of example, polymers with multiple-bound HLE inhibitory agents provide an opportunity to incorporate several inhibitory moieties into a single unit, thereby increasing the efficiency of the transfer of the inhibitory agent to the active site of the enzyme. This, in turn, optimizes the affinity of the polymer-bound inhibitor towards the enzyme when compared with the low-molecular weight HLE inhibitory agent itself.

The HLE inhibitory agents are prepared as is taught by the art. By means of example, a group of derivatized oligopeptides having HLE inhibitory activity may be prepared as described in U.S. Pat. Nos. 4,643,991; 5,162,307; and 5,008,245 all to Digenis et al.

The loading of the HLE inhibitory agents onto the polymers either alone or by means of a linker or spacer is conducted by chemical reactions which are known in the art and need not be described here in detail. The degree of loading, i.e., density of the HLE inhibitory units along the polymeric chain can be varied in a way such that it is most appropriate in accordance with the loading desired. This can be attained by varying the experimental conditions, e.g., the number of appended HLE active moieties on the polymeric chain, the number of spacer groups and/or the ratio of HLE inhibitory groups to the polymer in the reaction. Examples of these are shown in the examples of U.S. Pat. No. 5,162,307 to Digenis et al. However, other means can also be utilized for adjusting the density of the inhibitory units along the polymeric chain as is known in the art.

In a preferred embodiment of the invention, the method is practiced subsequent to an ocular operation, and the corneal scarring or fibroblast proliferation is therefore post-operative. In another particular embodiment, the method of the invention is applied to corneal scarring or fibroblast proliferation which is associated with ocular conjunctivitis or other ocular infections or biological damage.

In another embodiment of the invention the method is applied to corneal scarring or fibroblast proliferation associated with corneal burning or other heat-associated damage of the eye.

In still another embodiment, the method of the invention is applied to corneal scarring or fibroblast proliferation which is associated with mechanical injury or chemical injury.

The method of the invention may be practiced by applying the HLE inhibitory agent topically, intraocularly, by injection or through a contact lens. Preferred is topical application.

Typically, the HLE inhibitory agent is applied as a composition comprising an about 0.001–99.9 wt. % aqueous solution of the agent, preferably about 0.01–99 wt. % solution of the agent, and more preferably about 0.1–90 wt. % solution thereof. Most preferably, the inhibitory agent is applied in accordance with the present invention as a composition comprising an aqueous solution containing about 1–10 wt. % of the agent. Other amounts however may also be utilized. The composition may also contain other ingredients known as useful in ocular treatments. These are additives which are known in the art.

In still another embodiment of the invention the above method may be applied as a preventative method to a subject who is susceptible to the ocular condition.

The HLE inhibitory agent may be applied to the eye of a subject at varied intervals of time. Typically, the interval of time will depend on the residence time of the inhibitory agent in the eye. Thus, polymer-bound agents are "longer acting" and need not be reapplied for longer periods of time than free agents as is known in the art. Typically, polymer-bound HLE inhibitory agents may be applied every about 24 hours to seven days, and in some instances even longer periods of time. The free HLE inhibitory agents may be reapplied every about one hour to 24 hours. However, other intervals are utilized as suitable for specific HLE inhibitory agents and ocular conditions. Also part of this invention is a method of reducing neovascularization of corneal scar tissue or fibroblast proliferation comprising applying to an area of a subject's eye afflicted with the condition a neovascularization-inhibitory amount of a human leukocyte elastase (HLE) inhibitory agent under conditions and for a period of time effective to attain the desired effect.

Typically, the application is conducted for a few days to up to a few months, and sometimes for longer periods of time as needed to attain the desired result.

As in the case of the prior method the HLE inhibitory agent may be selected from the group consisting of free and water-soluble polymer-bound HLE inhibitory agents described above and/or known in the art.

The method described herein may also be practiced by applying the inhibitory agent to corneal scarring or fibroblast proliferation associated with post-operative conditions. Thus, the agent may be applied immediately after surgery, or as soon as ocular bleeding stops.

In another embodiment the corneal scarring or fibroblast proliferation to which the method is applied is associated with ocular conjunctivitis or other ocular infections or biological damage. In this case, the corneal scarring is produced by injury associated with microorganisms lodged in the ocular cavity and/or tissues. The ocular composition may in such cases additionally contain an antibiotic or other drug for the purpose of fighting the infection as well. In another embodiment, the method the invention may be applied to corneal scarring or fibroblast proliferation which is associated with corneal burning or heat-coagulation injuries.

In still another embodiment the method may be practiced on corneal scarring or fibroblast proliferation which is associated with mechanical injury of the eye, e.g., mechanical injury of the ocular cornea.

In still another embodiment the corneal scarring or fibroblast proliferation the method is applied to is associated with chemical injury. This typically occurs by exposure of the eye, and particularly the cornea, to chemical products which have a detrimental effect on ocular tissues.

In one embodiment of this method of the invention the HLE inhibitory agent may be applied topically, intraocularly, by injection or through a contact lens. Preferred is the topical application of an ocular composition, e.g., a solution of the agent. By means of example a composition comprising an aqueous solution of the compound may be applied to the eye as an about 0.001–99.9 wt. % solution thereof, preferably about 0.01–99 wt. %, and more preferably about 0.1–90 wt. %. A most preferred composition comprises a solution of the HLE inhibitory agent of about 1–10 wt. % thereof.

In still another embodiment, this method of the invention is a preventative method wherein the HLE inhibitory agent is applied to a subject susceptible to the condition prior to its occurrence.

Having now generally described this invention, the same will be better understood by reference to certain specific examples, which are included herein for purposes of illustration only and are not intended to be limiting of the invention or any embodiment thereof, unless so specified.

EXAMPLES

Example 1: Chemicals and Solutions

The following two representative compounds, KY7-11A and KY-3-PC5, compounds A and B, respectively, were tested for use in the methods of the invention.

TABLE 1

Exemplary HLE Inhibitory Agents Utilized

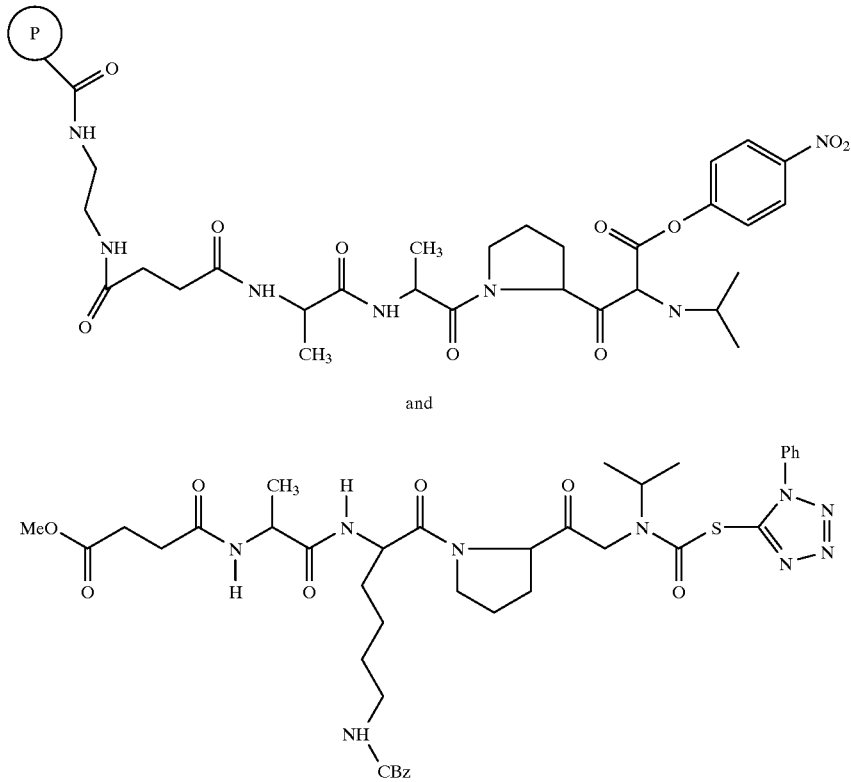

and

Compound 1 is a peptidyl carbamate elastase (HLE) inhibitor which is chemically bound to a non-biodegradable water soluble polymer with an average molecular weight of about 1,000 to 5000,000 daltons. This compound is described in U.S. Pat. No. 5,162,307. Compound 2 is a peptidyl carbamate elastase (HLE) inhibitor and is representative of a large series of peptidyl carbamate HLE inhibitors described in U.S. Pat. No. 5,008,245.

Example 2: Solutions Tested (1) Solution A: Control

This solution consists of normal saline (0.9% NaCl) and contains 1.4% w/V of polyvinyl alcohol. This solution was used as a control.

(2) Solution B:

This solution contains the active elastase inhibitory agent (Compound 1 or Compound 2) at a concentration of 10 $\mu$g/mL. The inhibitory agent was dissolved in normal saline (0.9% NaCl) containing 1.4% w/v of polyvinyl alcohol.

(3) Solution C:

This solution contains the elastase inhibitory agent Compound 2 at a concentration of 50 $\mu$g/mL. This inhibitory agent was dissolved in normal saline (0.9% NaCl) containing 1.4% w/v of polyvinyl alcohol.

All the above solutions were freshly made immediately prior to conducting the tests. The samples were then kept under refrigeration at 5° C.

Example 3: Animal Experiments

All surgery was performed by a Board-certified ophthalmologist (M.D.). Sedation and euthanasia were performed by a veterinarian (DVM) ophthalmologist (M.D.) under aseptic conditions. Histopathology was conducted by an expert pathologist (M.D.) at the University of Miami, School of Medicine, Miami, Fla. and the Pathology Laboratory at the Ophthalmology Department at the University of Iowa, Iowa City, Iowa.

All samples were coded and all the above mentioned operators had no knowledge of the key to the code (blind test).

Example 4: General Animal Preparation 26 rabbits were tranquilized with acetylpromazine maleate, 16 mg/kg intramuscularly. 2% lidocaine HCl eye drops were instilled in each eye for corneal anesthesia. Once the corneas were anesthetized, an eyelid speculum was inserted and the lids were then separated.

The corneas of each eye were thermally coagulated with the tip of a battery-powered ophthalmic cautery. A burn measuring 3 mm in diameter was placed near the superior limbus of each eye.

Two drops of solution A, B or C were instilled in designated treated eyes every 15 min for 6 hrs., then every 2 hrs. for 12 hrs. Following this, two eye drops of the same solutions were instilled four times a day. Daily eye examination was performed and photographs were taken.

Two weeks after treatment the rabbits were sacrificed by longer intracardiac injection of T-61 (50 $\mu$mg/kg). Subsequently, the rabbits, eyeballs were enucleated, the globes placed in Bounri's solution (10% formalin solution) and submitted for histopathology cell analysis.

Example 5: Histopathological Results

The eyes were fixed with 10% formalin solution and labeled right (R) and left (L), as appropriate sectioned and stained with H & E (hematoxylin & eosin stains). Histological sections were read by a pathologist without knowledge of the previously undertaken experimental procedure (blind test).

Table 2 below shows typical results obtained from a minimum of six (6) rabbits per treatment.

TABLE 2

Microscopic Description of Rabbit Eyes

| Treatment | Results |
|---|---|
| Untreated Solution A (normal saline & 1.4% w/v polyvinyl alcohol) | Eyes (the untreated ones) showed an area, 5–6 mm in extent, and involving the entire thickness of the cornea, of vascular and fibroblastic proliferation with an intense inflammatory infiltrate consisting predominantly of eosinophils, with very few plasma cells and lymphocytes. In that area the surface epithelium was ulcerated. The deeper one half of the cornea showed almost a pure fibroblastic proliferation with collagen deposition. In most of the cases an intense stromal vascularization with central scarring and the presence of numerous polymorphonuclear leukocytes, were observed. |
| Treated with Solution B (10 μg/ml of Compounds 1 or 2) | The reaction is not quite as intense as in the untreated specimen. Toward the periphery of the specimen, of corneal vascularization and migration fibroblasts into the cornea, was or observed. Centrally, there was a zone of superficial scarring, just beneath the corneal epithelium. Superficially, a zone of proliferating fibroblasts around the carotid collagen, was also noticed. |
| Treated with Solution C (50 μg/ml Comp. B) | In contrast to the "untreated" eyes, the treated eyes (with Solution C) exhibited focal areas of subepithelial vascular proliferation of only 0.6–1.0 mm in extent and involved only one third of the corneal thickness. This represents a protection against scarring, due to corneal burns of a tenfold magnitude. |

The above histopathologic results show that after application of the solutions (Solution A, B or C), severe fibrosis and neovascularization was still present in the control or untreated corneas while very little neovascularization or fibrosis could be detected in the experimental corneas (especially those treated with solution C). Accordingly, ophthalmic solutions of Compound 1 or Compound 2, which are representative of a larger group of HLE inhibitory agents, are proven effective in reducing fibrosis, neovascularization and inflammation in corneal wound-healing.

The invention now being fully described, it will be apparent to one of ordinary skill in the art that many changes and modifications can be made thereto without departing from the spirit or scope of the invention as set forth herein.

We claim:

1. A method of reducing corneal scarring or fibroblast proliferation comprising administering to an area of a subject's eye afflicted with the condition a corneal scar-reducing or fibroblast proliferation-reducing amount of a human leukocyte elastase (HLE) inhibitory agent under conditions and for a period of time effective to attain a scar-reducing or fibroblast proliferation-reducing effect;

wherein the HLE inhibitory agent is selected from the group consisting of (a) carbamates substituted by oligopeptides and described by the following general formula (I):

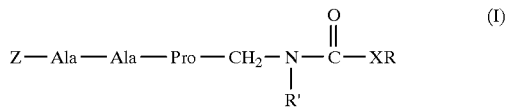

wherein Z is selected from the group consisting of R"O-Suc wherein

R" is lower alkyl of 1 to 3 carbon atoms, and $CF_3CO-$;
X is oxygen or sulfur; R' is selected from the group consisting of straight or secondary branched-chain alkyl of 1 to 4 carbon atoms, alkenyl of 1 to 4 carbon atoms, alkynyl of 2 to 4 carbon atoms; and cycloalkyl of 3 to 6 carbon atoms and R is selected from the group consisting of substituted or unsubstituted phenyl wherein the substituents are selected from the group consisting of nitro, fluoro, benzyl, $CH_2CF_2CF_2CF_3$, 1-lower alkyl tetrazolyl-, 1-phenyltetrazolyl-, 2-thioxo-3-thiazolindyl, pyridyl, and benzothiazolyl, provided that when R is p-nitrophenyl, R' is other than tertiary-butyl, benzyl or cyclohexyl, and when X is sulfur, R is other than benzyl;

(b) a polymer of the formula

wherein
P is a polymer comprising at least one unit of the formula $(A_mB_n)$, wherein $(A_mB_n)$ are substantially nonbiodegradable polymer units and has an average molecular weight of about 1,000 to 500,000 daltons, m and n may be the same or different and are about 5 to 3,000, and A and B may be the same or different and at least one of A and B is capable of covalently binding to one of L and $R^4$;
wherein $R^4$ is selected from the group consisting of:
   (i) a substituent C of the formula;

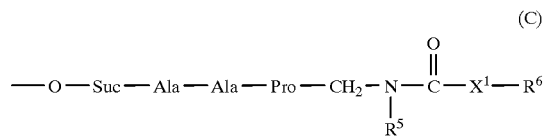

wherein
$X^1$ is oxygen or sulfur,
$R^5$ is selected from the group consisting of straight and secondary branch-chained $(C_1-C_4)$ alkyl, $(C_2-C_3)$ alkenyl, $(C_2-C_4)$ alkynyl, $(C_3-C_6)$ cycloalkyl, and benzyl,
$R^6$ is selected from the group consisting of substituted and unsubstituted phenyl, wherein the substituents are selected from the group consisting of nitro, pentafluoro, benzyl, $CH_2CF_2CF_2CF_3$, 1-lower alkyl tetrazolyl, 1-phenyltetrazolyl, 2-thioxo-3-thiazolidinyl-, pyridyl and benzothiazolyl, provided that when $R^6$ is p-nitrophenyl, $R^5$ is other than tert-butyl, benzyl or cyclohexyl, and when $X^1$ is sulfur, $R^6$ is other than benzyl;

(ii) a substituent D of the formula

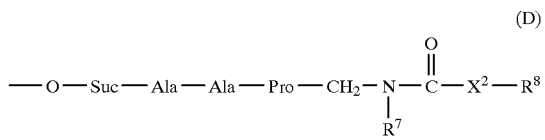

wherein $X^2$ is O or S, $R^8$ is selected from the group consisting of phenyl, nitrophenyl, fluorophenyl, —$CH_2CF_2CF_2CF_3$, 1-lower alkyltetrazolyl, 1-phenyltetrazolyl, benzyl, 2-thioxo-3-thiazolidinyl, pyridyl and benzothiazolyl; and $R^7$ is selected from the group consisting of straight or secondary branch chained ($C_1$–$C_4$) alkyl, ($C_2$–$C_3$) alkenyl, ($C_2$–$C_4$) alkynyl, ($C_3$–$C_6$) cycloalkyl, and benzyl, provided that when $R^8$ is p-nitrophenyl, $R^7$ is other than tertiary-butyl, benzyl or cyclohexyl, and when $X^2$ is sulfur, $R^8$ is other than benzyl; and (iii) a substituent E of the formula

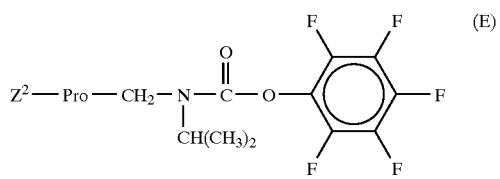

wherein $Z^2$ is —O—Suc-Ala-Ala;

each said $R^4$ being covalently bound to L or to one of A and B,

L is selected from the group consisting of a covalent bond and a linker group which is covalently bound to $R^4$ and one of A and B; and q is about 1 to m+n; and (c) a compound selected from the group consisting of a compound of the formula

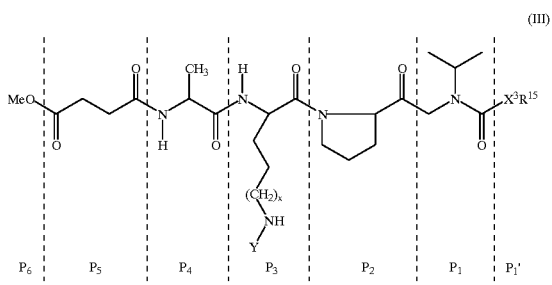

and a compound of the formula

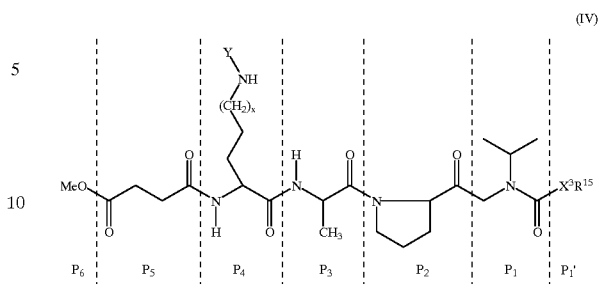

wherein

X is 1 or 2;

Y is carbobenzoxy or benzoyl; and $X^3R^{15}$ in formulae (III) and (IV) is

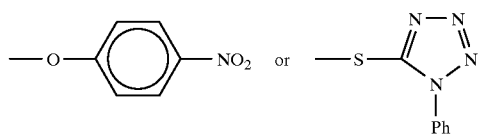

and $P_6$, $P_5$, $P_4$, $P_3$, $P_2$, $P_1$ and $P_1{'}$ define regions of formulae (III) and (IV).

2. The method of claim 1, wherein
the corneal scarring or fibroblast proliferation is postoperative.

3. The method of claim 1, wherein
the corneal scarring or fibroblast proliferation is associated with ocular infection.

4. The method of claim 1, wherein
the corneal scarring or fibroblast proliferation is associated with corneal burning.

5. The method of claim 1, wherein
the corneal scarring or fibroblast proliferation is associated with mechanical injury.

6. The method of claim 1, wherein
the corneal scarring or fibroblast proliferation is associated with chemical injury.

7. The method of claim 1, wherein the inhibitory agent is applied topically.

8. The method of claim 1, wherein
the inhibitory agent is applied as an about 0.001 to 99.9% aqueous solution.

9. The method of claim 1, wherein
the corneal scarring or fibroblast proliferation is postoperative.

10. The method of claim 1, wherein
the corneal scarring or fibroblast proliferation is associated with ocular infection.

11. The method of claim 1, wherein
the corneal scarring or fibroblast proliferation is associated with corneal burning.

12. The method of claim 1, wherein
the corneal scarring or fibroblast proliferation is associated with mechanical injury.

13. The method of claim 1, wherein
the corneal scarring or fibroblast proliferation is associated with chemical injury.

14. A method of reducing neovascularization of corneal scar tissue comprising administering to an area of a subject's eye a neovascularization-inhibitory amount of an HLE inhibitory agent under conditions and for a period of time effective sufficient to reduce neovascularization of corneal scar tissue wherein the HLE inhibitor agent is selected from the group consisting of
(a) carbamates substituted by oligopeptides and described by the following general formula (I):

$$Z-Ala-Ala-Pro-CH_2-N(R')-C(=O)-XR \quad (I)$$

wherein Z is selected from the group consisting of R"O-Suc- where R" is lower alkyl of 1 to 3 carbon atoms, and $CF_3CO-$; X is oxygen or sulfur; R' is selected from the group consisting of straight or secondary branched-chain alkyl of 1 to 4 carbon atoms, alkenyl of 1 to 4 carbon atoms, alkynyl of 2 to 4 carbon atoms; and cycloalkyl of 3 to 6 carbon atoms, and R is selected from the group consisting of substituted or unsubstituted phenyl wherein the substituents are selected from the group consisting of nitro, fluoro, benzyl, $CH_2CF_2CF_2CF_3$, 1-lower alkyl tetrazolyl-, 1-phenyltetrazolyl-, 2-thioxo-3-thiazolindyl, pyridyl, and benzothiazolyl, provided that when R is paranitrophenyl, R' is other than tertiary-butyl, benzyl or cyclohexyl, and when X is sulfur, R is other than benzyl;

(b) a polymer of the formula $$P-(L-R^4)_q$$

wherein

P is a polymer comprising at least one unit of the formula $(A_mB_n)$, wherein $(A_mB_n)$ are substantially nonbiodegradable polymer units and has an average molecular weight of about 1,000 to 500,000 daltons, m and n may be the same or different and are about 5 to 3,000, and A and B may be the same or different and at least one of A and B is capable of covalently binding to one of L and $R^4$;

wherein $R^4$ is selected from the group consisting of
(i) a substituent C of the formula:

$$-O-Suc-Ala-Ala-Pro-CH_2-N(R^5)-C(=O)-X^1-R^6 \quad (C)$$

wherein $X^1$ is oxygen or sulfur;

$R^5$ is selected from the group consisting of straight and secondary branch-chained $(C_1-C_4)$ alkyl, $(C_2-C_3)$ alkenyl, $(C_2-C_4)$ alkynyl; and $(C_3-C_6)$ cycloalkyl, and benzyl, and $R^6$ is selected from the group consisting of substituted and unsubstituted phenyl, wherein the substituents are selected from the group consisting of nitro, pentafluoro, benzyl, $CF_2CF_2CF_2CF_3$, 1-lower alkyl tetrazolyl, 1-phenyltetrazolyl, 2-thioxo-3-thiazolidinyl-, pyridyl and benzothiazolyl, provided that when $R^6$ is p-nitrophenyl, $R^5$ is other than tert-butyl, benzyl or cyclohexyl, and when $X^1$ is sulfur, $R^6$ is other than benzyl;

(ii) a substituent D of the formula;

$$-O-Suc-Ala-Ala-Pro-CH_2-N(R^7)-C(=O)-X^2-R^8 \quad (D)$$

wherein $X^2$ is O or S, $R^8$ is selected from the group consisting of phenyl, nitrophenyl, fluorophenyl, $-CH_2CF_2CF_2CF_3$, 1-lower alkyltetrazolyl, 1-phenyltetrazolyl, benzyl, 2-thioxo-3-thiazolidinyl, pyridyl and benzothiazolyl, and $R^7$ is selected from the group consisting of straight or secondary branch chained $(C_1-C_4)$ alkyl, $(C_2-C_3)$ alkenyl, $(C_2-C_4)$ alkynyl; and $(C_3-C_6)$ cycloalkyl, and benzyl, provided that when $R^8$ is p-nitrophenyl, $R^7$ is other than tertiary-butyl, benzyl or cyclohexyl, and when $X^2$ is sulfur, $R^8$ is other than benzyl; and (iii) a substituent E of the formula $$Z^2-Pro-CH_2-N(CH(CH_3)_2)-C(=O)-O-C_6F_5 \quad (E)$$

wherein $Z^2$ is —O—Suc-Ala-Ala;

each said $R^4$ being covalently bound to L or to one of A and B,

L is selected from the group consisting of a covalent bond and a linker group which is covalently bound to $R^4$ and one of A and B; and q is about 1 to m+n; and (c) a compound selected from the group consisting of a compound of the formula (III)

and a compound of the formula

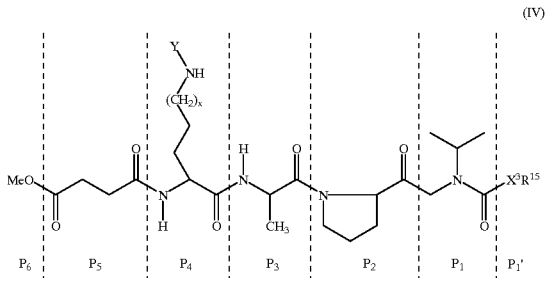

wherein
x is 1 or 2;
Y is carbobenzoxy or benzoyl; and
$X^3R^{15}$ in formulae (III) and (IV) is

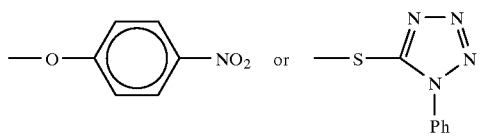

and $P_6$, $P_5$, $P_4$, $P_3$, $P_2$, $P_1$ and $P_1'$ define regions of the formulae (III) and (IV).

15. The method of claim 14, wherein the inhibitory agent is applied topically.

16. The method of claim 14, wherein
the inhibitory agent is applied as an about 0.001 to 99.9% aqueous solution.

17. A method of preventing corneal scarring or fibroblast proliferation comprising administering to an area of a subject's eye susceptible to the condition a corneal scar-reducing or fibroblast proliferation-reducing amount of an HLE inhibitory agent under conditions and for a period of time effective to prevent corneal scarring or fibroblast proliferation,
wherein the HLE inhibitory agent is selected from the group consisting of
(a) carbamates substituted by oligopeptides and described by the following general formula (I):

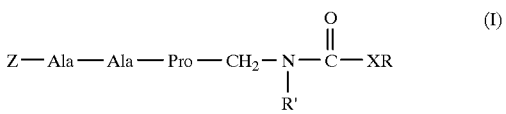

wherein Z is selected from the group consisting of R"O-Suc- where R" is lower alkyl of 1 to 3 carbon atoms, and $CF_3CO$—; X is oxygen or sulfur; R' is selected from the group consisting of straight or secondary branched-chain alkyl of 1 to 4 carbon atoms, alkenyl of 1 to 4 carbon atoms, alkynyl of 2 to 4 carbon atoms; and cycloalkyl of 3 to 6 carbon atoms; and R is selected from the group consisting of substituted or unsubstituted phenyl wherein the substituents are selected from the group consisting of nitro, fluoro, benzyl, $CH_2CF_2CF_2CF_3$, 1-lower alkyl tetrazolyl, 1-phenyltetrazolyl-, 2thioxo-3-thiazolindyl, pyridyl, and benzothiazolyl, provided that when R is paranitrophenyl, R' is other than tertiary-butyl, benzyl or cyclohexyl, and when X is sulfur, R is other than benzyl;

(b) a polymer of the formula $$P{-}(L{-}R^4)_q$$

wherein
P is a polymer comprising at least one unit of the formula $(A_mB_n)$, wherein $(A_mB_n)$ are substantially nonbiodegradable polymer units and has an average molecular weight of about 1,000 to 500,000 daltons, m and n may be the same or different and are about 5 to 3,000, and A and B may be the same or different and at least one of A and B is capable of covalently binding to one of L and $R^4$; wherein $R^4$ is selected from the group consisting of:
(i) a substituent C of the formula;

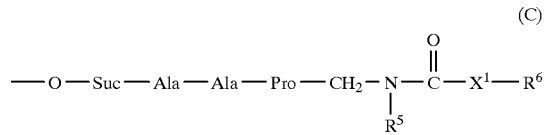

wherein
$X^1$ is oxygen or sulfur;
$R^5$ is selected from the group consisting of straight and secondary branch-chained $(C_1–C_4)$ alkyl, $(C_2–C_3)$ alkenyl, $(C_2–C_4)$ alkynyl; and $(C_3–C_6)$ cycloalkyl, and benzyl, and
$R^6$ is selected from the group consisting of substituted and unsubstituted phenyl, wherein the substituents are selected from the group consisting of nitro, pentafluoro, benzyl, $CH_2CF_2CF_2CF_3$, 1-lower alkyl tetrazolyl, 1-phenyltetrazolyl, 2-thioxo-3-thiazolidinyl-, pyridyl and benzothiazolyl, provided that when $R^6$ is p-nitrophenyl, $R^5$ is other than tert-butyl, benzyl or cyclohexyl, and when $X^1$ is sulfur, $R^6$ is other than benzyl;
(ii) a substituent D of the formula:

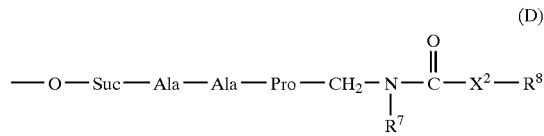

wherein
$X^2$ is O or S,
$R^8$ is selected from the group consisting of phenyl, nitrophenyl, fluorophenyl, $—CH_2CF_2CF_2CF_3$, 1-lower alkyltetrazolyl, 1-phenyltetrazolyl, benzyl, 2-thioxo-3-thiazolidinyl, pyridyl and benzothiazolyl,
$R^7$ is selected from the group consisting of straight or secondary branch chained $(C_1–C_4)$ alkyl, $(C_2–C_3)$ alkenyl, $(C_2–C_4)$ alkynyl; and $(C_3–C_6)$ cycloalkyl, and benzyl, provided that when $R^8$ is p-nitrophenyl, $R^7$ is other than tertiary-butyl, benzyl or cyclohexyl, and when $X^2$ is sulfur, $R^8$ is other than benzyl; and (iii) a substituent E of the formula

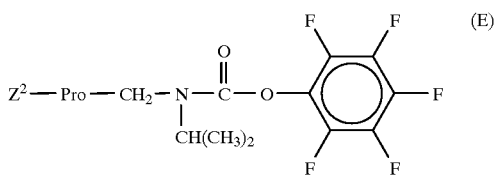

wherein
$Z^2$ is —O—Suc-Ala-Ala;
each said $R^4$ being covalently bound to L or to one of A and B,
L is selected from the group consisting of a covalent bond and a linker group which is covalently bound to $R^4$ and one of A and B; and
q is about 1 to m+n; and
(c) a compound selected from the group consisting of a compound of the formula

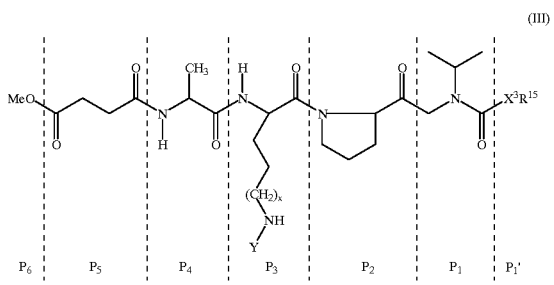

and
a compound of the formula

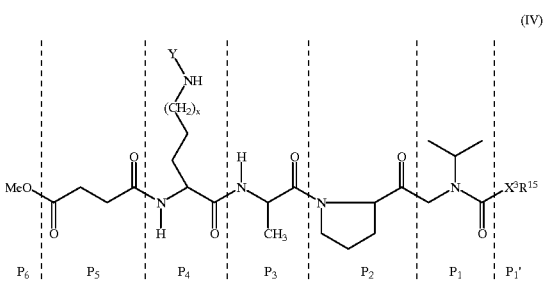

wherein
x is 1 or 2;
Y is carbobenzoxy or benzoyl; and
$X^3R^{15}$ in formulae (III) and (IV) is

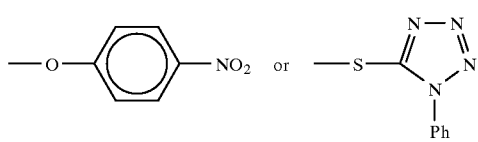

and $P_6$, $P_5$, $P_4$, $P_3$, $P_2$, $P_1$ and $P_1'$ define regions of the formulae (III) and (IV).

18. A method of preventing neovascularization of corneal scar tissue comprising administering to an area of a subject's eye a neovascularization-inhibitory amount of an HLE inhibitory agent under conditions and for a period of time effective to prevent neovascularization of corneal scar tissue wherein the HLE inhibitor agent is selected from the group consisting of
(a) carbamates substituted by oligopeptides and described by the following general formula (I):

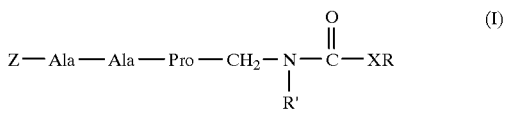

wherein Z is selected from the group consisting of R"O-Suc where R" is lower alkyl of 1 to 3 carbon atoms, an $CF_3CO—$; X is oxygen or sulfur; R' is selected from the group consisting of straight or secondary branched-chain alkyl of 1 to 4 carbon atoms, alkenyl of 1 to 4 carbons atoms, alkynyl of 2 to 4 carbon atoms; and cycloalkyl of 3 to 6 carbon atoms, and R is selected from the group consisting of substituted or unsubstituted phenyl wherein the substituents are selected from the group consisting of nitro, fluoro, benzyl, $CH_2CF_2CF_2CF_3$, 1-lower alkyl tetrazolyl-, 1-phenyltetrazolyl-, 2thioxo-3-thiazolindyl, pyridyl, and benzothiazolyl, provided that when R is para-nitrophenyl, R' is other than tertiary-butyl, benzyl or cyclohexyl, and when X is sulfur, R is other than benzyl;
(b) a polymer of the formula $$P—(L-R^4)_q$$

wherein
P is a polymer comprising at least one unit of the formula $(A_mB_n)$, wherein $(A_mB_n)$ are substantially non-biodegradable polymer units and has an average molecular weight of about 1,000 to 500,000 daltons, m and n may be the same or different and are about 5 to 3,000, and A and B may be the same or different and at least one of A and B is capable of covalently binding to one of L and $R^4$;
wherein $R^4$ is selected from the group consisting of:
(i) a substituent C of the formula

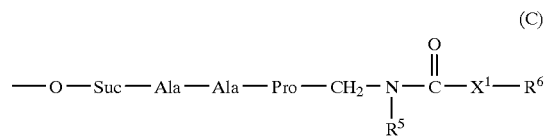

wherein
$X^1$ is oxygen or sulfur;
$R^5$ is selected from the group consisting of straight and secondary branch-chained $(C_1–C_4)$ alkyl, $(C_2–C_3)$ alkenyl, $(C_2–C_4)$ alkynyl; and $(C_3–C_6)$ cycloalkyl, and benzyl, and
$R^6$ is selected from the group consisting of substituted and unsubstituted phenyl, wherein the substituents are selected from the group consisting of nitro, pentafluoro, benzyl, $CH_2CF_2CF_2CF_3$, 1-lower alkyl tetrazolyl, 1-phenyltetrazolyl, 2-thioxo-3-thiazolidinyl-, pyridyl and benzothiazolyl, provided that when $R^6$ is p-nitrophenyl, $R^5$ is other than tert-butyl, benzyl or cyclohexyl, and when $X^1$ is sulfur, $R^6$ is other than benzyl;

(ii) a substituent D of the formula:

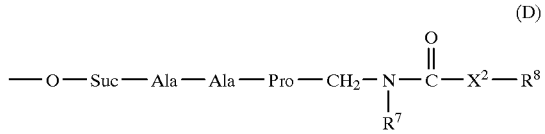
(D)

wherein $X^2$ is O or S, $R^8$ is selected from the group consisting of phenyl, nitrophenyl, fluorophenyl, —$CH_2CF_2CF_2CF_3$, 1-lower alkyltetrazolyl, 1-phenyltetrazolyl, benzyl, 2-thioxo-3-thiazolidinyl, pyridyl and benzothiazolyl, and $R^7$ is selected from the group consisting of straight or secondary branch-chained ($C_1$–$C_4$) alkyl, ($C_2$–$C_3$) alkenyl, ($C_2$–$C_4$) alkynyl; and ($C_3$–$C_6$) cycloalkyl, and benzyl, provided that when $R^8$ is p-nitrophenyl, $R^7$ is other than tertiary-butyl, benzyl or cyclohexyl, and when $X^2$ is sulfur, $R^8$ is other than benzyl; and (iii) a substituent E of the formula

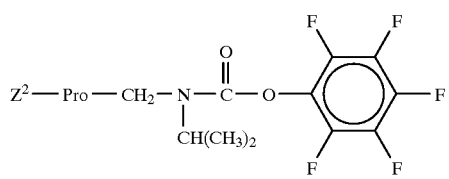
(E)

wherein $Z^2$ is —O—Suc-Ala-Ala;

each said $R^4$ being covalently bound to L or to one of A and B,

L is selected from the group consisting of a covalent bond and a linker group which is covalently bound to $R^4$ and one of A and B; and q is about 1 to m+n; and (c) a compound selected from the group consisting of a compound of the formula

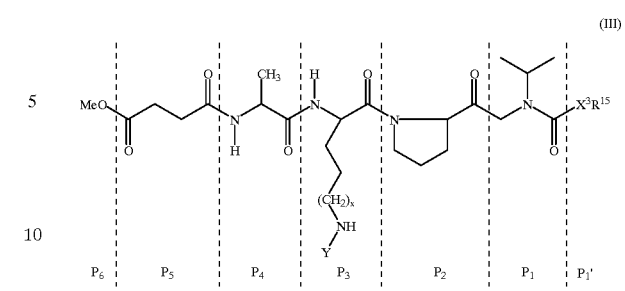
(III)

and a compound of the formula

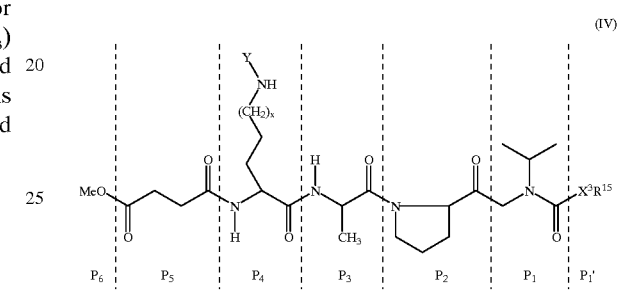
(IV)

wherein x is 1 or 2;

Y is carbobenzoxy or benzoyl; and $X^3R^{15}$ in formulae (III) and (IV) is

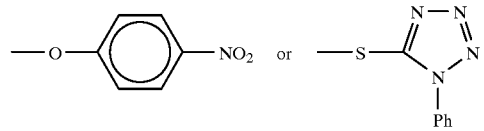

and $P_6$, $P_5$, $P_4$, $P_3$, $P_2$, $P_1$ and $P_1'$ define regions of the formulae (III) and (IV).

* * * * *